(12) United States Patent
Pellegrini et al.

(10) Patent No.: US 6,564,151 B1
(45) Date of Patent: May 13, 2003

(54) ASSIGNING PROTEIN FUNCTIONS BY COMPARATIVE GENOME ANALYSIS PROTEIN PHYLOGENETIC PROFILES

(75) Inventors: Matteo Pellegrini, Sherman Oaks, CA (US); Edward M. Marcotte, Los Angeles, CA (US); Michael J. Thompson, Santa Monica, CA (US); David Eisenberg, Los Angeles, CA (US); Robert Grothe, Santa Monica, CA (US); Todd O. Yeates, Agoura Hills, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/493,498

(22) Filed: Jan. 28, 2000

Related U.S. Application Data

(60) Provisional application No. 60/134,092, filed on May 14, 1999, provisional application No. 60/134,093, filed on May 14, 1999, provisional application No. 60/126,593, filed on Mar. 26, 1999, provisional application No. 60/118,206, filed on Feb. 1, 1999, and provisional application No. 60/117,844, filed on Jan. 29, 1999.

(51) Int. Cl.[7] .......................... G06F 19/00; G11C 17/00
(52) U.S. Cl. ........................................... 702/19; 365/94
(58) Field of Search ...................... 702/20, 19; 365/94

(56) References Cited

PUBLICATIONS

Dandekar et al. Conservation of gene order: a fingerprint of proteins that physically interact. Trends in Biochemical Sciences, vol. 23, pp. 324–328, (1998).*

Huynen et al, Measuring genome evolution, May 1998, Proc. Natl. Acad. Sci., USA, vol. 95, pp. 5849–5856.*

Gaasterland et al, Constructing Multigenome Views of Whole Microbial Genomes, 1998, Microbial & Comparative Genomics, vol. 3, No. 3, pp. 177–192.*

Marcotte et al., "A combined algorithm for genome–wide prediction of protein function," NATURE, GB, Macmillan Magazines Ltd., London, vol. 402, No. 6757, ISSN: 0028–0836, pp. 83–86, Nov. 4, 1999.

Marcotte et al., "Detecting Protein Function and Protein–Protein Interactions from Genome Sequences," SCIENCE, vol. 285, ISSN: 0036–8075, pp. 751–753, Jul. 30, 1999.

Pellegrini et al., "Assigning protein functions by comparative genome analysis: Protein phylogenetic profiles," Proceedings of the National Academy of Sciences, vol. 96, pp. 4285–4288, Apr. 1999.

Tatusov et al., "A Genomic Perspective on Protein Families," Science, US, American Association for the Advancement of Science, vol. 278, ISSN: 0036–8075, Oct. 24, 1997.

Enright et al., "Protein interaction maps for complete genomes based on gene fusion events," NATURE, Online, vol. 402, pp. 86–90, Nov. 4, 1999, Retrieved from the Internet on Jun. 22, 2000 <URL: www.nature.com>.

Pazos, et al., "Comparative analysis of different method for the detection of specificity regions in protein families," Biocomputing and Emergent Computation, Online, pp. 1–13, 1997. Retrieved from the Internet on Jun. 22, 2000 <URL:http://www.cnb.uam.es/{cnbprot/conf/TD.html>.

Eisen et al., "Cluster analysis and display of genome–wide expression patterns," Proceedings of the National Academy of Sciences, vol. 95, pp. 14863–14868, Dec. 1998.

* cited by examiner

*Primary Examiner*—John S. Brusca
(74) *Attorney, Agent, or Firm*—Fish & Richardson P.C.

(57) ABSTRACT

A computational method system, and computer program are provided for inferring functional links from genome sequences. One method is based on the observation that some pairs of proteins A' and B' have homologs in another organism fused into a single protein chain AB. A transgenome comparison of sequences can reveal these AB sequences, which are Rosetta Stone sequences because they decipher an interaction between A' and B. Another method compares the genomic sequence of two or more organisms to create a phylogenetic profile for each protein indicating its presence or absence across all the genomes. The profile provides information regarding functional links between different families of proteins. In yet another method a combination of the above two methods is used to predict functional links.

30 Claims, 17 Drawing Sheets

US 6,564,151 B1

ASSIGNING PROTEIN FUNCTIONS BY COMPARATIVE GENOME ANALYSIS PROTEIN PHYLOGENETIC PROFILES

CROSS REFERENCE TO RELATED APPLICATIONS

This application claims the benefit of Provisional Application Serial No. 60/117,844, filed Jan. 29, 1999, Provisional Application Serial No. 60/118,206, filed Feb. 1, 1999, Provisional Application Serial No. 60/126,593, filed Mar. 26, 1999, Provisional Applications Serial No. 60/134,093, filed May 14, 1999, and Provisional Application Serial No. 60/134,092, filed May 14, 1999, to which applications priority claim is made under 35 U.S.C. §119(e), the disclosures of which are incorporated herein by reference. The present application also incorporates by reference U.S. Pat. No. 6,466,874, for "A Rosetta Stone Method For Detecting Protein Function and Protein-Protein Interactions From Genome Sequences"and U.S. Pat. No. 09/493,401, for "Combined Computational Methods For Detecting Protein Function And Protein-Protein Interactions From Genome Sequences", filed concurrently on Jan. 28, 2000. Each of the aforementioned applications is explicitly incorporated herein by reference in their entirety and for all purposes.

STATEMENT AS TO FEDERALLY SPONSORED RESEARCH

The U.S. Government has certain rights in this invention pursuant to Grant Nos. DE-FC03-87ER60615 awarded by the Department of Energy and GM31299 awarded by the National Institute of Health.

FIELD OF THE INVENTION

The present invention relates to methods and system for predicting the function of proteins. In particular, the invention relates to materials, software, automated system, and methods for implementing the same in order to predict the function(s) of a protein.

BACKGROUND OF THE INVENTION

A central core of modern biology is that genetic information resides in a nucleic acid genome, and that the information embodied in such a genome (i.e., the genotype) directs cell function. This occurs through the expression of various genes in the genome of an organism and regulation of the expression of such genes. The expression of genes in a cell or organism defines the cell or organism's physical characteristics (i.e., its phenotype). This is accomplished through the translation of genes into proteins.

Proteins (or polypeptides) are linear polymers of amino acids. The polymerization reaction, which produces a protein, results in the loss of one molecule of water from each amino acid, and hence proteins are often said to be composed of amino acid "residues." Natural protein molecules may contain as many as 20 different types of amino acid residues, each of which contains a distinctive side chain. The particular linear sequence of amino acid residues in a protein defines the primary sequence, or primary structure, of the protein. The primary structure of a protein can be determined with relative ease using known methods.

In order to more fully understand and determine potential therapeutics, antibiotic and biologics for various organisms, efforts have been taken to sequence the genomes of a number of organisms. For example the Human Genome Project began with the specific goal of obtaining the complete sequence of the human genome and determining the biochemical function(s) of each gene. To date, the project has resulted in sequencing a substantial portion of the human genome (J. Roach, http://weber.u.Washington.edu/~roach/human_genome_progress2.html) (Gibbs, 1995). At least twenty-one other genomes have already been sequenced, including, for example, *M. genitalium* (Fraser et al., 1995), *M jannaschii* (Bult et al., 1996), *H. influenzae* (Fleischmann et al., 1995), *E. coli* (Blattner et al., 1997), and yeast (*S. cerevisiae*) (Mewes et al., 1997). Significant progress has also been made in sequencing the genomes of model organism, such as mouse, *C. elegans*, Arabadopsis sp. and *D. melanogaster*. Several databases containing genomic information annotated with some functional information are maintained by different organization, and are accessible via the internet, for example, http://wwwtigr.org/tdb; http://www.genetics.wisc.edu; http://genome-www.stanford.edu/~ball; http://hiv-web.lanl.gov; http://www.ncbi.nlm.nih.gov; http://www.ebi.ac.uk; http://Pasteur.fr/other/biology; and http://www.genome.wi.mit.edu. The raw nucleic acid sequences in a genome can be converted by one of a number of available algorithms to the amino acid sequences of proteins, which carry out the vast array of processes in a cell. Unfortunately, these raw protein sequence data do not immediately describe how the proteins function in the cell. Understanding the details of various cellular processes (e g., metabolic pathways, signaling between molecules, cell division, etc.) and which proteins carry out which processes, is a central goal in modern cell biology.

Throughout evolution, the protein sequences in different organisms have been conserved to varying degrees. As a result, any given organism contains many proteins that are recognizably similar to proteins in other organisms. Such similar proteins, having arisen from the same ancestral protein, are called homologs.

To a degree homology between proteins is useful in assigning biological functions to new protein sequences. The most direct approach for assigning functions to proteins is by laborious laboratory experimentation. However, if a particular uncharacterized protein sequence is homologous to one that has already been studied experimentally, often the function of the former can be equated to the function of the latter.

Unfortunately, the ability to assign functions to proteins by homology is limited. Many protein sequences do not have experimentally characterized homologs in other organisms. Depending on the organism, between one-third and one-half of the proteins in a genome cannot be assigned functions by homology or other available computational methods. Accordingly, new methods for predicting the functions of proteins from genome sequences are needed.

SUMMARY OF THE INVENTION

Determining protein functions from genomic sequences is a central goal of bioinformatics. Genomic sequences do not contain explicit information on the function of the proteins that they encode, yet this information is critical in medical and agricultural biotechnology. The invention provides materials, software, automated system, and methods that are useful for predicting protein function. Such information is useful, for example, for identifying new genes and identifying potential targets for pharmaceutical compounds.

In one embodiment, the invention provides a method to predict functional links (e.g., associations between proteins) based on the concept that proteins that function together in a pathway or structural complex can often be found in another organism fused together into a single protein. By identifying these patterns of relationship or gene fusion one can predict the interactions between unknown proteins based on the similar sequence information found in other related proteins (i.e., either functionally related or physically related). Through sequence comparison, one can identify a fused protein, termed herein the "Rosetta Stone" protein, which is similar over different regions to two distinct proteins that are not similar to each other. This establishes a functional link between two otherwise unrelated proteins. The inventors have discovered that proteins that can be associated together via the Rosetta Stone protein tend strongly to be functionally linked.

In another embodiment, the invention provides a computational method that detects proteins that participate in a common structural complex or metabolic pathway. Proteins within these groups are defined as "functionally-linked." Functionally-linked proteins evolve in a correlated fashion, and therefore they have homologs in the same subset of organisms. For instance, it is expected that flagellar proteins will be found in bacteria that possess flagella but not in other organisms. Simply put, if two proteins have homologs in the same subset of fully (or nearly fully) sequenced organisms but are absent in other organisms they are likely to be functionally-linked. The present invention provides a method wherein this property is used to systematically map functional interactions between all the proteins coded by a genome. This method overcomes the problems wherein pairs of functionally linked proteins in general have no amino acid sequence similarity with each other and therefore cannot be linked by conventional sequence alignment techniques.

One embodiment provides a method of identifying multiple polypeptides as functionally-linked, the method including aligning a primary amino acid sequence of multiple distinct non-homologous polypeptides to the primary amino acid sequences of a plurality of proteins; and for any alignment found between the primary amino acid sequences of all of such multiple distinct non-homologous polypeptides and the primary amino acid sequence of at least one such protein, outputting an indication identifying the at least one such protein as an indication of a functional link between the multiple polypeptides.

In another embodiment, a computer program is provided for identifying a protein as functionally linked, the computer program comprising instructions for causing a computer system to align a primary amino acid sequence of multiple distinct non-homologous polypeptides to the primary amino acid sequences of a plurality of proteins; and for any alignment found between the primary amino acid sequences of all polypeptides and the primary amino acid sequence of an at least one such protein, output an indication of an identity of such protein.

In yet another embodiment, the invention provides a method of identifying a plurality of polypeptides as having a functional link, the method including aligning a primary amino acid sequence of a protein to the primary amino acid sequences of each of a plurality of distinct non-homologous polypeptides; and for any alignment found between the primary amino acid sequence of the protein and the primary amino acid sequence of the plurality of distinct non-homologous polypeptides, wherein the primary amino acid sequence of the protein contains an amino acid sequence similar to at least two distinct non-homologous polypeptides, outputting an indication identifying any distinct non-homologous polypeptides as functionally-linked.

In another embodiment the invention provides a computer program, stored on a computer-readable medium, for identifying a plurality of polypeptides as having a functional link, the computer program comprising instructions for causing a computer system to align a primary amino acid sequence of a protein to the primary amino acid sequences of each of a plurality of distinct non-homologous polypeptides; and for any alignment found between the primary amino acid sequences of the protein and the primary amino acid sequence of the plurality of distinct non-homologous polypeptides, wherein the primary amino acid of the protein contains an amino acid sequence from at least two distinct non-homologous polypeptides, and output an indication identifying any distinct non-homologous polypeptides as functionally-linked.

In yet another embodiment, the invention provides a method for identifying multiple proteins as having a functional link, comprising obtaining data, comprising a list of proteins from at least two genomes; comparing the list of proteins to form a protein phylogenetic profile for each protein or protein family, wherein the protein phylogenetic profile indicates the presence or absence of a protein belonging to a particular protein family in each of the at least two genomes based on homology of the proteins; and grouping the list of proteins based on similar profiles, wherein proteins with similar profiles are indicated to be functionally linked.

In yet still another embodiment, the invention provides a computer program, stored on a computer-readable medium, for identifying multiple polypeptides as having a functional link, the computer program comprising instructions for causing a computer system to obtain data, comprising a list of proteins from at least two genomes; compare the data to form a protein phylogenetic profile for each protein or protein family, wherein the protein phylogenetic profile indicates the presence or absence of a protein belonging to a particular protein family in each of the at least two genomes based on homology of the proteins; and group the list of proteins based on similar profiles, wherein proteins with similar profiles are indicated to be functionally linked.

In yet another embodiment, the invention provides a method for determining an evolutionary distance between two proteins, the distances being used as additional information, beyond mere presence or absence from a genome, in comparing the phylogenetic profiles of different proteins. The method including aligning two sequences; determining an evolution probability process by constructing a conditional probability matrix: $p(aa \rightarrow aa')$, where aa and aa' are any amino acids, said conditional probability matrix being constructed by converting an amino acid substitution matrix from a log odds matrix to said conditional probability matrix; accounting for an observed alignment of the constructed conditional probability matrix by taking the product of the conditional probabilities for each aligned pair during the alignment of the two sequences, represented by $$P(p) = \prod_n p(aa_n \rightarrow aa'_n)$$

and determining an evolutionary distance $\alpha$ from powers equation: $p' = p^\alpha(aa \rightarrow aa')$, maximizing for P. In a further embodiment, the conditional probability matrix is defined by a Markov process with substitution rates, over a fixed time interval.

In yet a further embodiment, the invention provides a method for determining functional links between at least two polypeptides, comprising aligning a primary amino acid sequence of multiple distinct non-homologous polypeptides to the primary amino acid sequences of a plurality of proteins; for any alignment found between the primary amino acid sequences of all of such multiple distinct non-homologous polypeptides and the primary amino acid sequence of at least one such protein, outputting an indication identifying the at least one such protein as an indication of a functional link between the multiple polypeptides; obtaining data, comprising a list of polypeptides from at least two genomes; comparing the list of polypeptides from at least two genomes to form a protein phylogenetic profile for each protein or protein family, wherein the protein phylogenetic profile indicates the presence or absence of a polypeptide belonging to a particular protein family in each of the at least two genomes based on homology of the polypeptides; grouping the list of polypeptides based on similar profiles, wherein a similar profile is indicative of a functional link between the polypeptides; and comparing the functional links identified above to determine common links.

In yet another embodiment, the invention further provides for displaying the functional links as networks of related proteins comprising placing all polypeptides in a diagram such that functionally linked proteins are closer together than all other proteins and identifying proteins that fall in a cluster in the diagram as a functionally related group.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION OF THE INVENTION

Figure 1A:
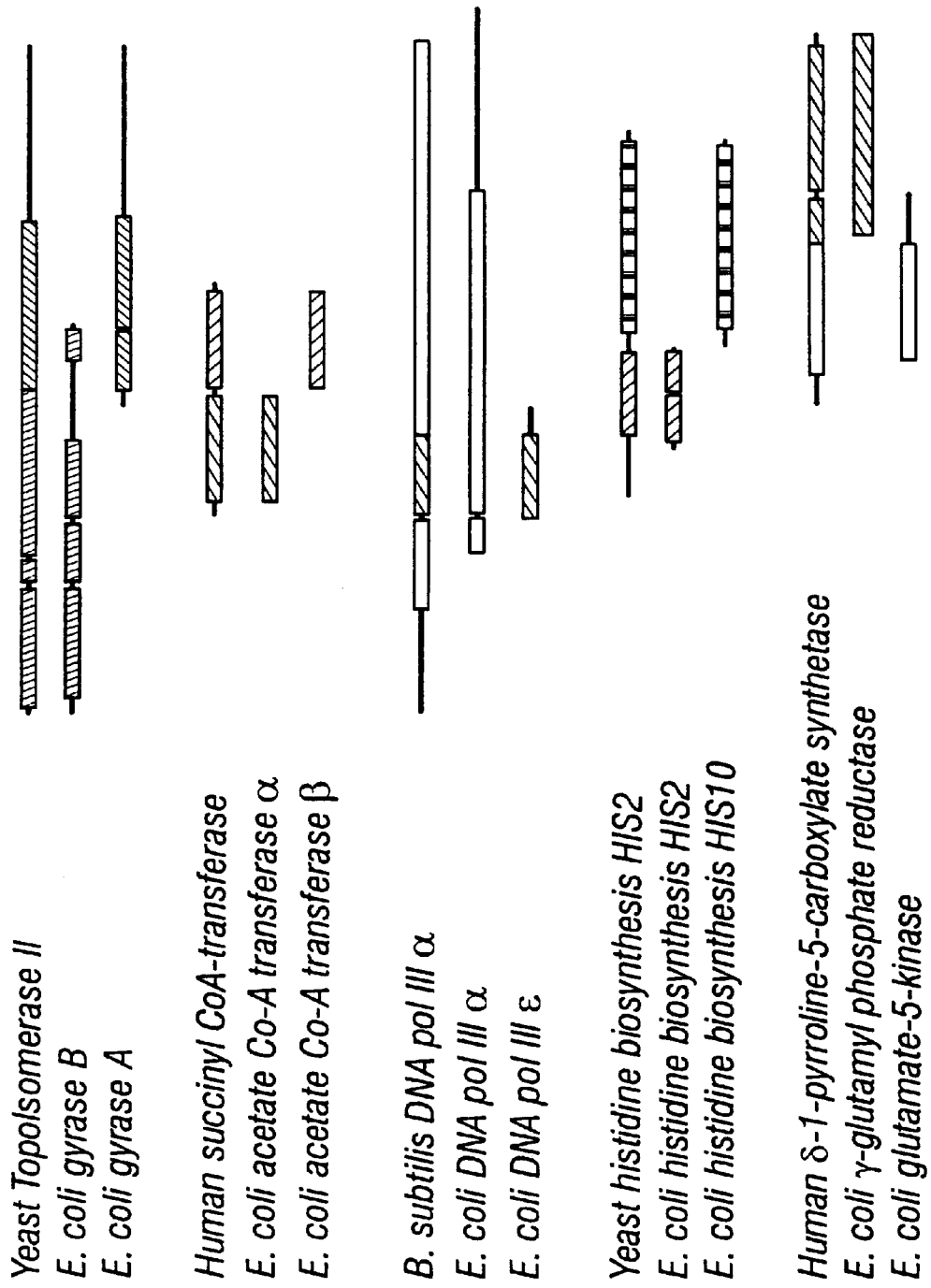
FIG. 1A shows five examples of pairs of E. coli proteins predicted to be functionally-linked by the Rosetta Stone method. In each example, the top protein is the "Rosetta Stone protein" and the bottom two proteins are functionally linked.

As used herein and in the appended claims, the singular forms "a," "and," and "the" include plural referents unless the context clearly dictates otherwise. Thus, for example, reference to "a protein" includes a plurality of proteins and reference to "the polypeptide" generally includes reference to one or more polypeptides and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference in full for the purpose of describing and disclosing the databases, proteins, and methodologies, which are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

Definitions

The following terms have the following meanings when used herein and in the appended claims. Terms not specifically defined herein have their art recognized meaning.

An "amino acid" is a molecule having the structure wherein a central carbon atom (the α-carbon atom) is linked to a hydrogen atom, a carboxylic acid group (the carbon atom of which is referred to herein as a "carboxyl carbon atom"), an amino group (the nitrogen atom of which is referred to herein as an "amino nitrogen atom"), and a side chain group, R. When incorporated into a peptide, polypeptide, or protein, an amino acid loses one or more atoms of its amino acid carboxylic groups in the dehydration reaction that links one amino acid to another. As a result, when incorporated into a protein, an amino acid is referred to as an "amino acid residue."

"Protein" refers to any polymer of two or more individual amino acids (whether or not naturally occurring) linked via a peptide bond, and occurs when the carboxyl carbon atom of the carboxylic acid group bonded to the α-carbon of one amino acid (or amino acid residue) becomes covalently bound to the amino nitrogen atom of amino group bonded to the α-carbon of an adjacent amino acid. The term "protein" is understood to include the terms "polypeptide" and "peptide" (which, at times may be used interchangeably herein) within its meaning. In addition, proteins comprising multiple polypeptide subunits (e.g., DNA polymerase III, RNA polymerase II) or other components (for example, an RNA molecule, as occurs in telomerase) will also be understood to be included within the meaning of "protein" as used herein. Similarly, fragments of proteins and polypeptides are also within the scope of the invention and may be referred to herein as "proteins."

A particular amino acid sequence of a given protein (i.e., the polypeptide's "primary structure," when written from the amino-terminus to carboxy-terminus) is determined by the nucleotide sequence of the coding portion of a mRNA, which is in turn specified by genetic information, typically genomic DNA (including organelle DNA, e.g., mitochondrial or chloroplast DNA).

A "functional link" or "functionally-linked polypeptides" is meant polypeptides that are predicted to be linked, for example, in a common biochemical or metabolic pathway, part of a related protein complex, physically interact, or act upon one another.

ROSETTA STONE METHOD

This method compares proteins sequences across all known genomes and finds cases where proteins that are separate in one organism (or separately contained in two different organisms) are joined into one larger protein in another organism. In such cases, the two separate proteins often carry out related or sequential functions or form part of a larger protein complex. Therefore, the general function of one component (e.g., one or more of the unknown proteins) can be inferred from the function of the other component if it is known. In addition, merely identifying links between proteins using the method described herein provides valuable information regardless of whether the function of one or more of the proteins used to form the link(s) is known. The two components do not have similar amino acid sequence, so the function of one would not be inferred from the other on the basis of sequence similarity-alone.

The methods described herein (i.e., the "Rosetta Stone Method") is based on the idea that proteins that participate in a common structural complex, metabolic pathway, biological process or with closely related physiological functions are functionally linked. In addition, the method is also capable of identifying proteins that interact physically with one another. Functionally linked proteins in one organism can often be found fused into a single polypeptide chain in a different organism. Similarly, fused proteins in one organism can be found as individual proteins in other organisms. For example, in a first organism, or in two separate organisms, one might identify two un-linked proteins "A" and "B" with unknown function. In another organism, one may find a single protein "AB" with a part that resembles "A" and a part that resembles "B". Protein AB allows one to predict that "A" and "B" are functionally-related.

The particular functions activity of each distinct protein in the Rosetta Stone method need not be known prior to performing the method (i.e., the function of A, B, or AB need not be known). Performing the Rosetta Stone method with unknown proteins can provide information regarding relationships of each protein absent knowledge of the functional activity of the proteins themselves. For example, the information (i.e., the links) can provide information that the proteins are part of a common pathway, function in a related process or physically interact. Such information need not be based on the biological functions of the individual proteins. The method of the invention can provide information regarding functional links between proteins not previously known to function together,for example, in a concerted process. A marker, for example, for a particular disease state is identified by the presence or absence of a protein (e.g., Her2/neu in breast cancer detection). Links (i.e., information) identified by the methods of the invention, which link proteins "B" and "C" to such a marker suggest that proteins "B" and "C" are related by function, physical interaction or are part of a common biological pathway with the marker. Such information is useful in making diagnostics, identifying drug targets and therapeutics. Accordingly, the Rosetta Stone method of the invention is performed by sequence comparison that searches for incomplete "triangle relationships" between, for example, three proteins, i.e., for two proteins A' and B' that are different from one another but similar in sequence to another protein AB. Completing the triangle relationship provides useful information regarding the proteins' biological function; functional interaction, pathway relationships or physical relationships with other proteins in the "triangle".

Figure 1B:
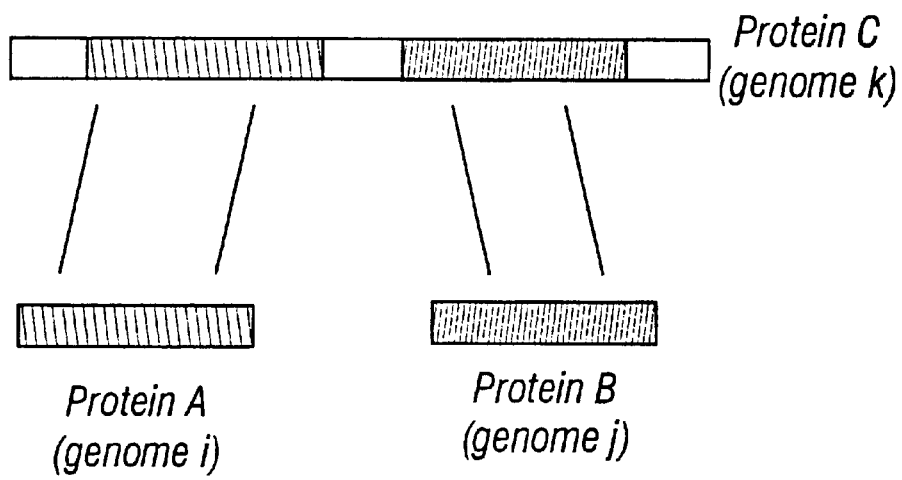
FIG. 1B shows the Rosetta-Stone analysis finds cases where a protein (c) is similar over different regions to two distinct, non-homologous proteins (A and B). In such situations, a functional relationship is inferred between A and B. Genomes i,j, and k can represent a single genome, or two or three different genomes.

As an example, FIG. 1 shows five examples of pairs of *E. coli* proteins predicted to interact by the domain fusion analysis (i.e., the Rosetta Stone method). Each protein is shown schematically with boxes representing domains (as defined in the ProDom domain database). For each example, a triplet of proteins is pictured. The second and third proteins are predicted to interact because their homologs are fused in the first proteins (called the Rosetta Stone protein). The first three predictions are known to interact from experiments (Sugino et al. Nucleic Acids Res. 8, 3865 (1980); Yeh and Ornston, J. Biol. Chem., 256, 1565 (1981); McHenry and Crow, J. Biol. Chem, 254, 1748 (1979)). The final two examples show pairs of proteins from the same pathway (two nonsequential enzymes from the histidine biosynthesis pathway and the first two steps of the proline biosynthesis pathway) that are not known to interact directly. The inventors have recognized that when this pattern of three proteins exists—two separate proteins from a first organism (or from two distinct organisms) that are homologous to different portions of a single protein from another organism—the two separate proteins are usually "functionally-related" based on the data showing they have a higher than random chance of being physically or functionally linked. Accordingly, the invention overcomes the shortfalls of previous methods by providing a relationship between the linked proteins found by the Rosetta Stone Method though they do not have amino acid sequence similarity with each other and therefore cannot be linked by conventional sequence alignment techniques.

The methods of the invention are applicable to both nucleotide sequences and amino acid sequences. Typically amino acid sequences will be used to perform the methods of the invention. However, where a nucleic sequence is to be used it is typically translated from a nucleic acid sequence to amino acid sequence. Such translation may be performed in all frames of the nucleic acid sequence if the coding sequence is not known. Programs that can translate a nucleic acid sequence are known in the art. In addition, for simplicity, the description of the invention discusses the use of a "pair" of proteins in the determination of a Rosetta Stone protein, more than 2 (e.g., 3, 4, 5, 10, 100 or more proteins) may be used. Accordingly, one can analyze chains of linked proteins, such as "A" linked by a Rosetta Stone protein to "B" linked by a Rosetta Stone protein to "C", etc. By this method, groups of functionally related proteins can be found and their function identified.

In one embodiment the method of the invention starts with identifying the primary amino acid sequence for a plurality of proteins whose functional relationship is to be determined (e.g., protein A' and protein B'). A number of source databases are available, as described above, that contain either a nucleic acid sequence and/or a deduced amino acid sequence for use with the first step of the invention. All sequences to be tested (the "probe sequences") are used to search a sequence database (e.g., GenBank, PFAM or ProDom), either simultaneously or individually. Every protein in the sequence database is examined for its ability to act as a Rosetta Stone protein (i.e., a single protein containing polypeptide sequences or domains from both protein A' and protein B'). A number of different methods of performing such sequence searches are known in the art. Such sequence alignment methods include, for example, BLAST (Altschul et al., 1990), BLITZ (MPsrch) (Sturrock & Collins, 1993), and FASTA (Person & Lipman, 1988). The probe sequence can be any length (e.g., about 50 amino acid residues to more than 1000 amino acid residues).

Probe sequences (e.g., polypeptide sequences or domains) found in a single protein (e.g., AB protein) are defined as being "linked" by that protein. Pairs of probe sequences are used individually to search the sequence database, one can mask those segments having homology to the first probe sequence found in the proteins of the sequence database prior to searching with the subsequent probe sequence. In this way, one eliminates any potential overlapping sequences between the two or more probe sequences.

The linked proteins can then be further compared for similarity with one another by amino acid sequence comparison. Where the sequences have high homology, such a finding can be indicative of the formation of homo-dimers, -trimer, etc. Typically, Rosetta Stone linked proteins are only kept when the linked proteins show no homology to one another (e.g., hetero-dimers, trimer etc.).

In another embodiment of the method of the invention, a potential fusion protein lacking any functional information and that is suspected of having two or more domains (e.g., a potential Rosetta Stone Protein) may be used to search for related proteins by a similar method. In this embodiment, the primary amino acid of the fusion protein is determined and used as a probe sequence. This probe sequence is used to search a sequence database (e.g., GenBank, PFAM or ProDom). Every protein in the sequence database is examined for homology to the potential fusion protein (i.e., multiple proteins containing polypeptide sequences or domains from the potential fusion protein). A number of different methods of performing such sequence searches are known in the art (e.g., BLAST, BLITZ (MPsrch), and FASTA). Probe sequences found in a more than one protein (e.g., A' and B' proteins) are defined as being "linked" so long as at least one protein per domain containing that domain but not the other is also identified. In other words, at least one protein or domain of the plurality of proteins must also be found alone in the sequence database. This verifies that the protein or domain is not an integral part of a first protein but rather a second independent protein having its own functional characteristics.

Statistical methods can be mused to judge the significance of possible matches. The statistical significance of an alignment score is described by the probability, P, of obtaining a higher score when the sequences are shuffled. One way to compute a P value threshold is to first consider the total number of sequence comparisons that are to be performed. If there are N proteins in $E.$ $coli$ and M in all other genomes this number is N×M. If a comparison of this number of random sequences would result in one pair to yield a P value of 1/NM by chance, this then is set as the threshold. The threshold may be set lower or higher according to the accuracy desired.

The method of the invention provides information regarding which proteins are functionally related (e.g., related biological functions, common structural complexes, metabolic pathways, signaling pathways, or other biological process) a subset of which proteins physically interact in an organism.

Figure 2A:
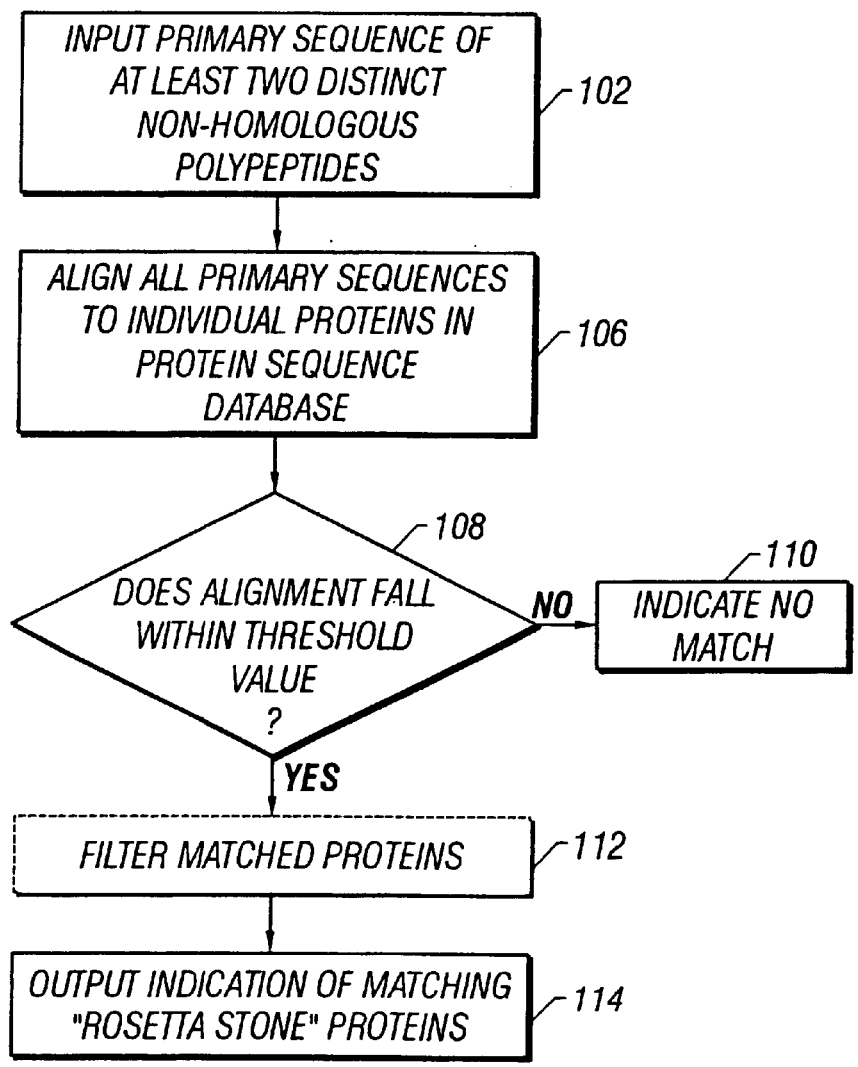
FIG. 2A is a flow diagram describing a Rosetta Stone method of the invention beginning with the primary sequence of at least two polypeptides having unknown function.

FIG. 2 is an operational flow diagram generally illustrating two embodiments of the invention. FIGS. 2A and B depict the use of Rosetta Stone proteins to predict the functional link or relationship of proteins. Referring now to FIG. 2A, in step 102 the primary amino acid sequence of at least two distinct non-homologous polypeptides is input into a computer. The biological function of the two polypeptides may be known or may be unknown. The primary sequence of the polypeptides may be input manually (i.e., by typing the sequence into a computer) or may be derived from a database of proteins or nucleic acid sequence available through various databases as described above. "Substantially homologous" means that the p value of the alignment score is statistically significant. A number of publicly available alignment programs can be used to determine the homology including, for example, BLAST and FASTA. A comparison of the polypeptide sequences can be performed to insure that the polypeptides are non-homologous. As a result only proteins having distinct non-homologous polypeptide domains will be used for further analysis.

In step 106, the input polypeptide sequences having distinct non-homologous polypeptide domains are aligned with the sequences contained in a protein sequence database. The proteins may have known or unknown biological functions. Examples of databases with protein sequences include for example, GenBank, PFAM, SwissProt or ProDom. Every protein in the sequence database is examined for homology to the first and second proteins. A number of different methods of performing such sequence searches are known in the art (e.g., BLAST, BLITZ,(MPsrch), and FASTA). Typically, the matches are determined by p value thresholds, as identified above and depicted at step 108. If there are no matches found, this determination is indicated at step 110. The input polypeptide sequences may be aligned simultaneously with the proteins of the database or they may be aligned sequentially. In a sequential alignment, those proteins having a match to a previously aligned polypeptide can be masked. Matches of proteins from the database containing sequences from all the polypeptides input at step 102 (e.g., both containing sequences from both protein A and protein B, i.e., the Rosetta Stone protein(s)) are identified, a list compiled and the function of any matched proteins indicated at step 114. Where the function of a matched protein is known, this function is used to determine possible functions of the unknown polypeptide sequences. Alternatively, following alignment and compilation of matched proteins, the matched proteins may be further filtered at step 112, as described below (see Filtering Methods). The inventors have discovered that proteins that can be associated together via the Rosetta Stone protein tend strongly to be functionally linked.

Figure 2B:
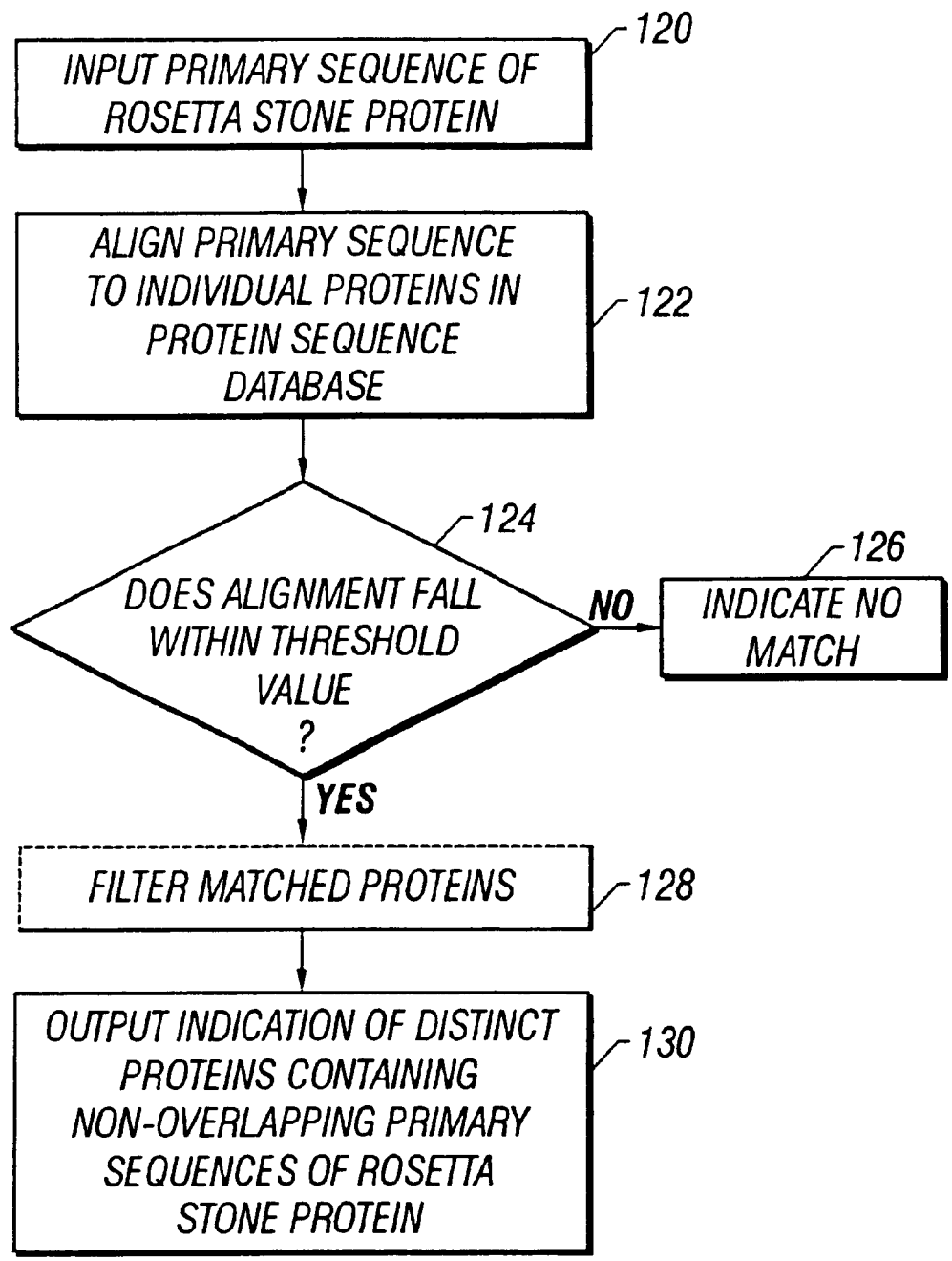
FIG. 2B is a flow diagram describing a method of the invention beginning with the primary sequence of a Rosetta Stone protein having unknown function.

Referring now to FIG. 2B, an alternative method for determining functional links of a protein is provided. In this embodiment, one starts with a potential Rosetta Stone protein and works in reverse. In step 120, the primary amino acid sequence of a Rosetta Stone protein is input into the computer. The primary sequence of the protein may be input manually (i.e., by typing the sequence into a computer) or may be derived from a database of proteins or nucleic acid sequence available to the public through various databases as described above.

In step 122, the protein sequence is aligned with a database of protein sequences. Every protein in the sequence database is examined for homology to domains of Rosetta stone protein. A number of different methods of performing such sequence searches are known in the art,(e.g., BLAST, BLITZ (MPsrch), and FASTA). Typically, matches are determined by p value thresholds, as identified above and depicted at step 124. If there are no matches found this determination is indicated at step 126. A list of distinct matched proteins are compiled and indicated at step 130. In order to insure that the distinct non-homologous polypeptides align to the Rosetta Stone protein in a non-overlapping fashion the distinct polypeptides can be compared to determine homology. This insures identification of at least one protein per domain containing that domain, but not the other domain. In other words, at least one protein or domain of the unknown proteins in the database must also be found alone in the sequence database. This verifies that the first matched protein is not homologous to the second matched protein.

Alignment Algorithms

To align sequences a number of different procedures can be used that produce a good match between the corresponding residue in the sequences. Typically, Smith-Waterman or Needleman-Wunsch algorithms are used. However, as discussed above faster procedures such as BLAST, FASTA, PSI-BLAST can be used.

Filtering Methods

The Rosetta Stone Method described herein provides at least two pieces of information. First the method provides information regarding which proteins are functionally related. Second the method provides information regarding which proteins are physically related. Each of these two pieces of information has different sources of error and prediction. The first type of error is introduced by protein sequences that occur in many different proteins and paired with many other protein sequences. The second type of error is introduced due to there often being multiple copies of similar proteins, called paralogs, in a single organism. In general, the Rosetta Stone Method predicts functionally related proteins well, with no filtering of results required. However, it is possible to filter the error associated with either the first or second type of information.

The inventors recognized that a few domains are linked to an excessive number of other domains by a Rosetta Stone protein. The inventors recognized, for example, that 95% of the domains linked to fewer than 13 other domains. However, some domains (e.g., the Src Homology 3 (SH3) domain or ATP-binding cassette (ABC domains)) link to more than a hundred other domains. These links were filtered by removing all links generated involving these 5% of domains (i.e., the domains linked to more than 13 other domains). For example, in *E. coli*, without filtering, 3531 links were identified using the domain-based analysis, but after filtering only 749 links were identified. This method improved prediction of functionally related proteins by 28% and physically related proteins by 47%. Accordingly, there are a number of ways to filter the results to improve the significance of the functional links. As described above, as the number of functional links increases there is a increased higher chance of finding a Rosetta Stone proteins. By reducing the excessively linked proteins one reduces the chance number of Rosetta Stone proteins and thus increase the significance of a functional link.

In addition it was recognized that error introduced by multiple paralogs of linked proteins should have little effect on functional prediction, as paralogs usually have very similar function, but will affect the reliability of prediction of protein-protein interactions. This estimate is calculated for each linked protein pair, and can be estimated roughly as:

$$\text{Fractional Error} = 1 - \frac{\sqrt{N}}{N},$$

where N is the number of paralogous protein pairs, (e.g., A linked to B, A' linked to B', A linked to B', and A' linked to B, in the case that A and A' are paralogs, as are B and B', and the linking protein is AB as above).

The error can also be estimated as 1−T, where T is the mean percent of potential true positives calculated for all domain pairs in an organism. For each domain pair linked by a Rosetta Stone protein, there are n proteins with the first domain but not the second, and m proteins with the second domain but not the first. The percent of true positives T is therefore estimated as the smaller of n or m divided by n times m. As this error 1−T can be calculated for each set of linked domains, it can describe the confidence in any particular predicted interaction.

In addition, the error in functional links can be caused by small conserved regions or repeated common amino acid sequences being repeatedly identified in a Rosetta Stone protein by a plurality of distinct non-homologous polypeptides. To reduce this error the alignment percentage—the fraction of an entire sequence that can be aligned to another—between the Rosetta Stone and the distinct non-homologous polypeptide can be measured. Alignment percentages of about 50 to 90%, more typically about 75%, between the Rosetta Stone and the distinct polypeptide are indicative of the links that are not subject to the small peptide sequence.

PHYLOGENETIC PROFILE METHOD

The phylogenetic profile method compares protein sequences across all or many known genomes and analyzes the pattern of inheritance of each protein across the different organisms. In its simplest form, each protein is simply characterized by its presence or absence in each organism. For example, if there are 16 known genomes, then each protein may be assigned a 16-bit code or phylogenetic profile. Since proteins that function together (e.g., in the same metabolic pathway or as part of a larger structural complex) evolve in a correlated fashion, they should have the same or similar patterns of inheritance, and therefore similar phylogenetic profiles. Therefore, the function of one protein may be inferred from the function of another protein, which has a similar profile, if its function is known. As with the Rosetta Stone method (above), the function of one protein is inferred from the function of another protein which is dissimilar in sequence. Furthermore, even if neither of the two proteins has an assigned function, the predicted link between the proteins has utility in developing, for example, diagnostics and therapeutics. The phylogenetic profile method can be implemented in a binary code (i.e., describing the presence or absence of a given protein in, an organism) or a continuous code that describes how similar the related sequences are in the different genomes. In addition, grouping of similar protein profiles may be made wherein similar profiles are indicative of functionally related proteins. Furthermore, the requirements for similarity can be modified depending upon particular criteria by varying the difference in similar bit requirements. For example, criteria requiring that the degree of similarity in the profile include all 16 bits being identical can be set, but may be modified so that similarity in 15 bits of the 16 bits would indicate relatedness of the protein profiles as well. Statistical methods can be used to determine how similar two patterns must be in order to be related.

The phylogenetic profile method discussed is applicable to any genome including viral, bacterial, archaeal or eukaryotic. The method of phylogenetic profile grouping provides the prediction of function for a previously uncharacterized protein(s). The method also allows prediction of new functional roles for characterized proteins. It also provides potential informative connections (i.e., links) between uncharacterized proteins.

Figure 3:
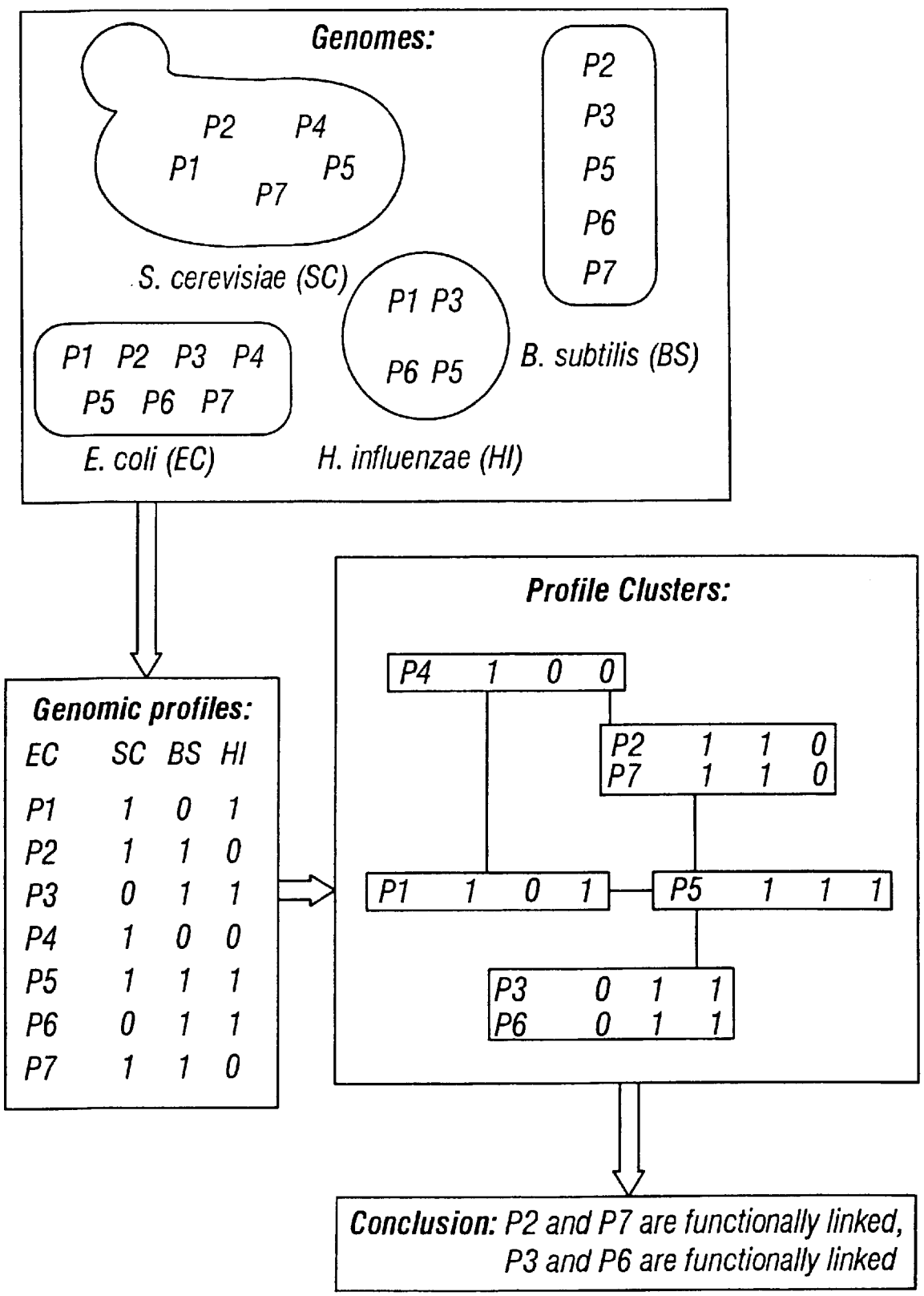
FIG. 3 is a schematic of phylogenetic pathways. P1 through P7 are distinct non-homologous proteins.

The method of protein phylogenetic profiles is illustrated schematically in FIG. 3 for the hypothetical case of four fully sequenced genomes, in which the functional relationship of seven proteins (P1 through P7) is described. For each hypothetical *E. coli* protein a profile was constructed, indicating which genomes code for homologs of the protein. A cluster or group of the profiles was created to determine which proteins share the same profiles. Proteins with identical (or similar) profiles are boxed to indicate that they are likely to be functionally linked. Boxes connected by lines have phylogenetic profiles that differ by one bit and are termed neighbors.

In one embodiment a computational method detects proteins that participate in a common structural complex or metabolic pathway. Proteins within these groups are defined as "functionally-linked" in that functionally-linked proteins evolve in a correlated fashion, and therefore have homologs in the same subset of organisms. For example, flagellar proteins are found in bacteria that possess flagella but not in other organisms. Accordingly, if two proteins have homologs in the same subset of fully sequenced organisms they are likely to be functionally linked. The methods of the invention use this concept to systematically map links between all the proteins coded by a genome. Typically, functionally linked proteins have no amino acid sequence similarity with each other and therefore cannot be linked by conventional sequence alignment techniques.

To represent the subset of organisms that contain a homolog a phylogenetic profile is constructed for each protein. The simplest manner to represent a protein's phylogenetic history is via a binary phylogenetic profile for each protein. This profile is a string with N entries, each one bit, where N corresponds to the number of genomes. The number of genomes can be any number of two or more (e.g., 2, 3, 4, 5, 10, 100, to 1000 or more). The presence of a homolog to a given protein in the $n^{th}$ genome is indicated with an entry of unity at the $n^{th}$ position (e.g., in a binary system an entry of 1). If no homolog is found the entry is zero. Proteins are clustered according to the similarity of their phylogenetic profiles. Similar profiles show a correlated pattern of inheritance, and by implication, functional linkage. The method predicts that the functions of uncharacterized proteins are likely to be similar to characterized proteins within a cluster (FIG. 3).

In order to decide whether a genome contains a protein related to another particular protein, the query amino acid sequence is aligned with each of the proteins from the genome(s) in question using known alignment algorithm (see above). To determine the statistical significance of any alignment score, the probability, p, of obtaining a higher score when the sequences are shuffled is described. One way to compute a p value threshold is to first consider the total number of sequence comparisons that are being aligned. If there are N proteins in a first organism's genome and M in all other genomes this number is N×M. If this number is compared to random sequences it would be expected that one pair would yield a p value of $$\frac{1}{NM}.$$

This value can be set as a threshold. Other thresholds may be used and will be recognized by those of skill in the art.

In another embodiment, a non-binary phylogenetic profile can be used. In this embodiment, the phylogenetic profile is a string of N entries where the $n^{th}$ entry represents the evolutionary distance of the query protein to the homolog in the $n^{th}$ genome. To define an evolutionary distance between two sequences an alignment between two sequences is performed. Such alignments can be carried out by any number of algorithms known in the art (for examples, see those described above). The evolution is represented by a Markov process with substitution rates, over a fixed interval of time, given by a conditional probability matrix:

$$p(aa \rightarrow aa')$$

where aa and aa' are any amino acids. One way to construct such a matrix is to convert the BLOSUM62 amino acid substitutions matrix (or any other amino acid substitution matrix, e.g., PAM100, PAM250) from a log odds matrix to a conditional probability (or transition) matrix:

$$P_B(i \rightarrow j) = p(j)2^{\wedge}\left[\frac{\text{BLOSUM62}ij}{2}\right] \quad (1)$$

P(i→j) is the probability that amino acid i will be replaced by amino acid j through point mutations according to the BLOSUM62 scores. The $p_j$'s are the abundances of amino acid j and are computed by solving the 20 linear equations given by the normalization conditions that:

$$\sum_i P_B(i \rightarrow j) = 1 \quad (2)$$

The probability of this process is computed to account for the observed alignment by taking the product of the conditional probabilities for each aligned pair:

$$P(p) = \prod_n p(aa_n \rightarrow aa'_n) \quad (3)$$

A family of evolutionary models is then tested by taking powers of the conditional probability matrix: $p' = p^{\alpha}(aa \rightarrow aa')$. The power, $\alpha$, that maximizes P is defined to be the evolutionary distance.

Many other schemes may be imagined to deduce the evolutionary distance between two sequences. For example, one might simply count the-number of positions in the sequence where the two proteins have adapted different amino acids.

Although the phylogenetic history of an organism can be presented as a vector (as described above), the phylogenetic profiles need not be vectors, but may be represented by matrices. This matrix includes all the pair wise distances between a group of homologous protein, each one from a different organism. Similarly, phylogenetic profiles could be represented as evolutionary trees of homologous proteins. Functional proteins could then be clustered or grouped by matching similar trees, rather than vectors or matrices.

In order to predict function, different proteins are grouped or clustered according to the similarity of their phylogenetic profiles. Similar profiles indicate a correlated pattern of inheritance, and by implication, functional linkage. The phylogenetic profile method predicts that the functions of uncharacterized proteins are likely to be similar to characterized proteins within a group or cluster.

Grouping or clustering may be accomplished in many ways. The simplest is to compute the Euclidean distance between two profiles. Another method is to compute a correlation coefficient to quantify the similarity between two profiles. All profiles within a specified distance of the query profile are considered to be a cluster or group.

Typically a genome database will be used as a source of sequence information. Where the genome database contains only a nucleic acid sequences the nucleic acid sequence is translated to an amino acid sequence in frame (if known) or in all frames if unknown. Direct comparison of the nucleic acid sequences of two or more organisms may be feasible but will likely be more difficult due to the degeneracy of the genetic code. Programs capable of translating a nucleic acid sequence are known in the art or easily programmed by those of skill in the art to recognize a codon sequence for each amino acid.

Figure 4A:
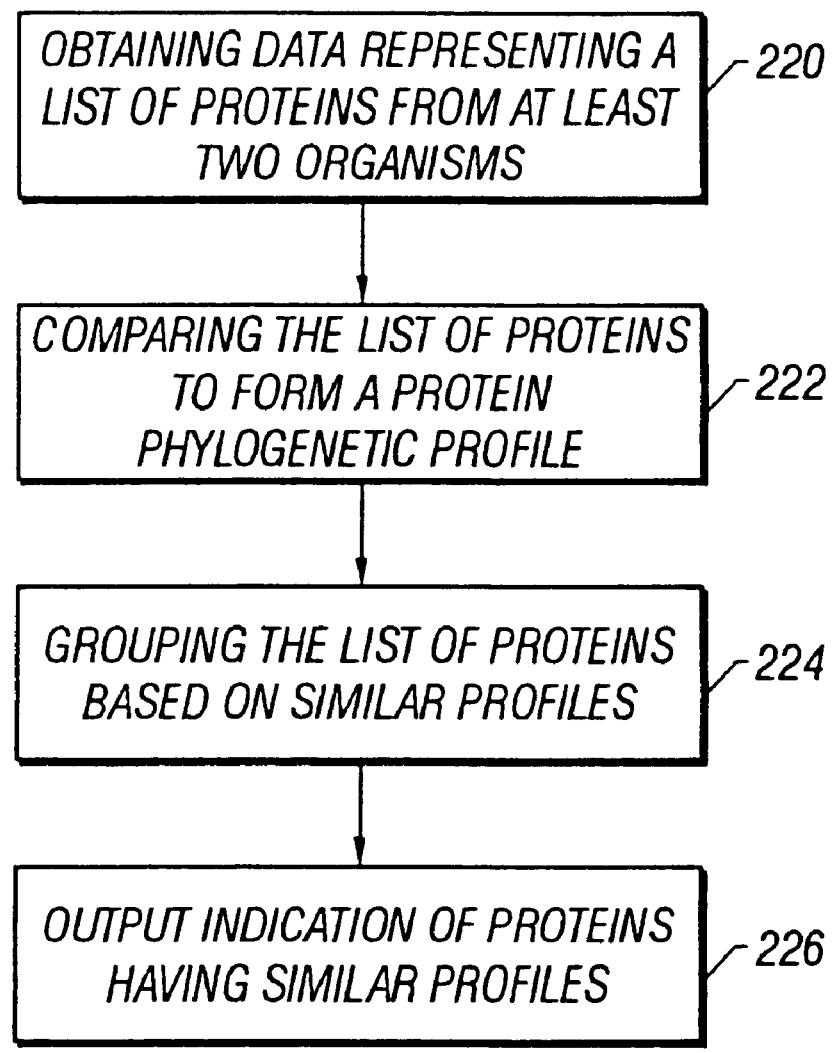
FIG. 4A shows a flow diagram describing a phylogenetic profile method of the invention using a bit type profiling method.

FIG. 4 depicts a flow diagram describing the basic algorithm used in determining functionally related proteins by the phylogenetic pathway method. Beginning with step 220 in FIG. 4A, data is obtained representing a list of proteins from at least two organisms. As described herein the data may be manually input or may be loaded or obtained from a database(s). The data typically will be in the form of amino acid sequence listings or nucleic acid sequence listings. At step 222, the list of proteins is compared to create a phylogenetic profile. The phylogenetic profile provides an indication of those proteins in each of the at least two organisms that share some degree of homology. Such a comparison can be done by any number of alignment algorithms known in the art or easily developed by one skilled in the art (see, for example, those listed above, e.g., BLAST, FASTA etc.) In addition, thresholds can be set regarding a required degree of homology. Each protein is then grouped at 224 with related proteins that share a similar phylogenetic profile. Grouping algorithms include, for example, those described herein. At 226 proteins sharing similar profiles are indicated and their known functions identified, if any.

Figure 4B:
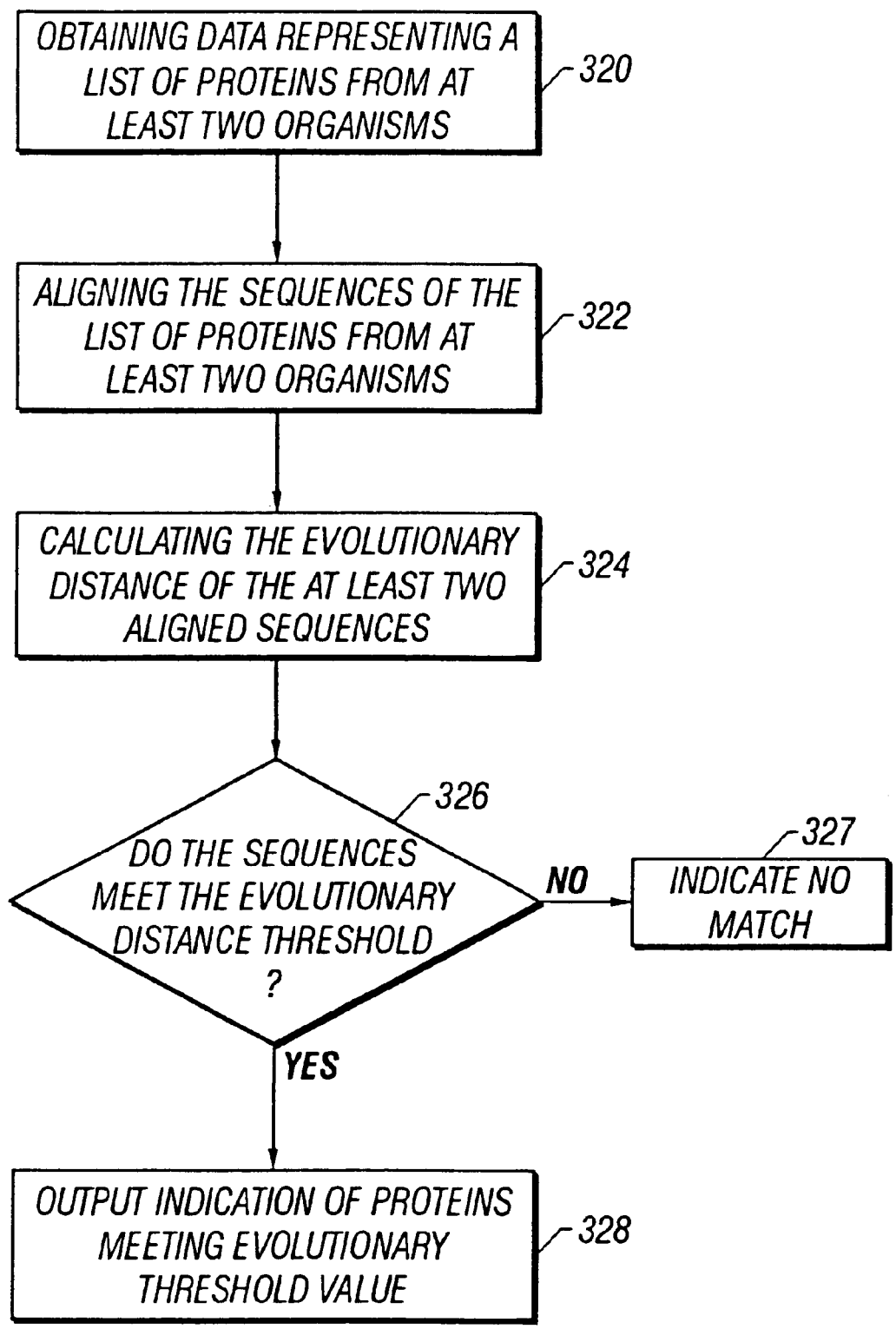
FIG. 4B shows a flow diagram describing a phylogenetic profile method of the invention using an evolutionary distance method.

With reference to FIG. 4B, a modification of the method of FIG. 4A is depicted. Beginning with step 320 in FIG. 4B, data is obtained representing a list of proteins from at least two organisms. As described herein the data may be manually input or may be loaded or obtained from a database. The data typically will be in the form of amino acid sequence listings or nucleic acid sequence listings. At step 322, the list of proteins is aligned between each protein in the input organisms. Such an alignment can be done by any number of alignment algorithms known in the art or easily developed by one skilled in the art (see, for example, those listed above, e.g., BLAST, FASTA etc.). At step 324, an evolutionary distance value is calculated by the methods described above. If the evolutionary distance threshold is met at step 326, those proteins meeting the evolutionary threshold value are identified at step 328, otherwise no match is indicated at step 327.

COMBINATION METHODS

Prediction of functionally linked proteins by the Rosetta Stone method can be filtered by other methods that predict functionally-linked proteins, such as the protein phylogenetic profile method or the analysis of correlated mRNA expression patterns. It was found that filtering by these two methods for the Rosetta Stone prediction for *S. cerevisiae*, that proteins predicted to be functionally linked by two or more of these three methods were as likely to be functionally related as proteins who were observed to physically interact by experimental techniques like yeast 2-hybrid methods or co-immunoprecipitation methods. Combinations of these methods of prediction can be used to establish functional links between proteins with very high confidence. The methods of the invention (i.e., the Rosetta Stone method and the Phylogenetic Profile method) can be combined with one another or with other protein prediction methods known in the art (see for example, Eisen et al., "Cluster analysis and display of genome-wide expression patterns," *Proc. Natl. Acad. Sci. USA*, 95:14863–8 (1998)).

COMPUTER IMPLEMENTATION

The various techniques, methods, and aspects of the invention described above can be implemented in part or in whole using computer-based systems and methods. Additionally, computer-based systems and methods can be used to augment or enhance the functionality described above, increase the speed at which the functions can be performed, and provide additional features and aspects as a part of or in addition to those of the invention described elsewhere in this document. Various computer-based systems, methods and implementations in accordance with the above-described technology are presented below.

The processor-based system can include a main memory, preferably random access memory (RAM), and can also include a secondary memory. The secondary memory can include, for example, a hard disk drive and/or a removable storage drive, representing a floppy disk drive, a magnetic tape drive, an optical disk drive, etc. The removable storage drive reads from and/or writes to a removable storage medium. Removable storage media represents a floppy disk magnetic tape, optical disk, etc., which is read by and written to by removable storage drive. As will be appreciated, the removable storage media includes a computer usable storage medium having stored therein computer software and/or data.

In alternative embodiments, secondary memory may include other similar means for allowing computer programs or other instructions to be loaded into a computer system. Such means can include, for example, a removable storage unit and an' interface. Examples of such can include a program cartridge and cartridge interface (such as the found in video game devices), a movable memory chip (such as an EPROM, or PROM) and associated socket, and other removable storage units and interfaces which allow software and data to be transferred from the removable storage unit to the computer system.

The computer system can also include a communications interface. Communications interfaces allow software and data to be transferred between computer system and external devices. Examples of communications interfaces can include a modem, a network interface (such as, for example, an Ethernet card), a communications port, a PCMCIA slot and card, etc. Software and data transferred via a communications interface are in the form of signals which can be electronic, electromagnetic, optical or other signals capable of being received by a communications interface. These signals are provided to communications interface via a channel capable of carrying signals and can be implemented using a wireless medium, wire or cable, fiber optics or other communications medium. Some examples of a channel can include a phone line, a cellular phone link, an RF link, a network interface, and other communications channels.

In this document, the terms "computer program medium" and "computer usable medium" are used to generally refer to media such as a removable storage device, a disk capable of installation in a disk drive, and signals on a channel. These computer program products are means for providing software or program instructions to a computer systems.

Computer programs (also called computer control logic) are stored in main memory and/or secondary memory. Computer programs can also be received via a communications interface. Such computer programs, when executed, enable the computer system to perform the features of the present invention as discussed herein. In particular, the computer programs, when executed, enable the processor to perform the features of the present invention. Accordingly, such computer programs represent controllers of the computer system.

In an embodiment where the elements are implemented using software, the software may be stored in, or transmitted via, a computer program product and loaded into a computer system using a removable storage drive, hard drive or communications interface. The control logic (software), when executed by the processor, causes the processor to perform the functions of the invention as described herein.

In another embodiment, the elements are implemented primarily in hardware using, for example, hardware components such as PALs, application specific integrated circuits (ASICs) or other hardware components. Implementation of a hardware state machine so as to perform the functions described herein will be apparent to person skilled in the relevant art(s). In yet another embodiment, elements are implanted using a combination of both hardware and software.

In another embodiment, the computer-based methods can be accessed or implemented over the World Wide Web by providing access via a Web Page to the methods of the present invention. Accordingly, the Web Page is identified by a Universal Resource Locator (URL). The URL denotes both the server machine, and the particular file or page on that machine. In this embodiment, it is envisioned that a consumer or client computer system interacts with a browser to select a particular URL, which in turn causes the browser to send a request for that URL or page to the server identified in the URL. Typically the server responds to the request by retrieving the requested page, and transmitting the data for that page back to the requesting client computer system (the client/server interaction is typically performed in accordance with the hypertext transport protocol ("HTTP")). The selected page is then displayed to the user on the client's display screen. The client may then cause the server containing a computer program of the present invention to launch an application, for example to perform a Rosetta Stone analysis or Phylogenetic Profile analysis based on a query sequence provided by the client.

The following examples are provided to illustrate the practice of the instant invention, and in no way limit the scope of the invention.

EXAMPLES

Rosetta Stone Method

Some interacting proteins such as the Gyr A and Gyr B subunits of *E. coli* DNA gyrase are fused into a single chain in another organism, in this case the topoisomerase II of yeast (Berger et al., Nature 379, 225 (1996)). Thus, the sequence similarities of Gyr A (804 amino acid residues) (and Gyr B (875 residues)) to different segments of the topoisomerase II (1429 residues)) suggest by the Rosetta Stone method that Gyr A and Gyr B interact in *E, coli.*

To find other such putative protein interactions in *E. coli*, 3000 (of the total of 4290) protein sequences of the *E. coli* genome (Blattner et al., Science 277, 1453 (1997)) were searched. The triplets of proteins are found with the aid of protein domain databases such as the ProDom or Pfam databases (Corpet et al. Nucleic Acids Res. 26, 323 (1998); Bateman et al., Nucleic Acids Res. 27, 260 (1999)). Here, a list of all ProDom domains in every one of the 64,568 SWISS-PROT proteins was prepared, as well as a list of all proteins that contain each of the 53,597 ProDom domains. Then every protein in ProDom was considered for its ability to be a linking or Rosetta Stone) member in a triplet. All pairs of domains that are both members of a given protein P were defined as being linked by a protein P, if at least one protein with only one of the two domains could be found. By this method 14,899 links between the 7843 ProDom damsons were found. Then in a single genome (such as *E. coli*) all non-homologous-pairs of proteins containing linked domains were found. These pairs are linked by the Rosetta Stone protein. For *E. coli*, this method found 3531 protein pairs. An alternate method for discovering protein triplets uses amino acid sequence alignment techniques to find two proteins that align to a Rosetta Stone protein such that the alignments do not overlap on the Rosetta Stone protein. For E. coli, this method found 4487 protein pairs, 1209 of which were also found by the ProDom search method (even though different sequence databases were searched for each method). 6809 pairs of non-homologous sequences, both members of the pair having significant similarity to a single protein in some other genome were found and termed Rosetta Stone sequences because the sequence was capable of deciphering the interaction between the protein pairs.

Each of these 6809 pairs is a candidate for a pair of interacting proteins in E. coli. Five such candidates are shown in FIG. 1. The first three pairs of E. coli proteins were among those easily determined from the biochemical literature in fact to interact. The final two pairs of proteins are not known to interact. They are representatives of many such pairs whose putative interactions at this time must be taken as testable hypotheses.

Three independent tests of interactions predicted by the Rosetta Stone method were devised, each showing that a reasonable fraction may in fact interact. The first method uses the annotation of proteins given in the SWISS-PROT database. For cases where the interacting proteins have both been annotated, we compare their annotations, looking for a similar function for both members of the pair. Similar function would imply at least a functional interaction. Of the 3950 E. coli pairs of known function, 2682 (68%) share at least one keyword in their SWISS-PROT annotations (ignoring the keyword "hypothetical protein"), suggesting related functional roles. When pairs of E. coli proteins are selected at random, only 15% share a key word. In short, of the E. coli pairs that the Rosetta Stone method turns up as candidates for protein-protein interactions, more than half have both members with a similar function; the method therefore seems to be a robust predictor of protein function. Where the function of one member of a protein pair is known, the function of the other member can be predicted. Performing a similar analysis in yeast turns up 45,502 protein pairs. Of the 9857 pairs of known function, 32% share at least one keyword in their annotations compared with 14% when proteins are selected at random.

The second test of the interactions predicted by the Rosetta Stone method uses as confirmation the Database of Interacting Proteins (http://doe-mbi.ucla.edu). This is a compilation of protein pairs that have been found to interact in some published experiment.

As of December 1998, the database contained 939 entries, 724 of which have both members of the pair listed in the ProDom database. Of these 724 pairs, we find 46 or 6.4% linked by Rosetta Stone sequences. We expect this percentage to rise as more genomes are sequenced, revealing more linked sequences.

The third test of Rosetta Stone predictors is by another computational method for predicting interactions (Pellegrini et al. PNAS 96, 4285 (1999)), the method of phylogenetic profiles, which detects functional interactions by correlated evolution of protein pairs. This method was applied to 6809 interactions predicted by the Rosetta Stone method for E. coli proteins. Some 321 of these (~5%) were suggested by the phylogenetic profile method to interact, more than eight times as many interaction in common as for randomly chosen sets of interactions. Given that the Rosetta Stone method and the phylogenetic profile method rest on entirely different assumptions, this level of overlap of predictions tends to support the predictive power of both methods.

Figure 5:
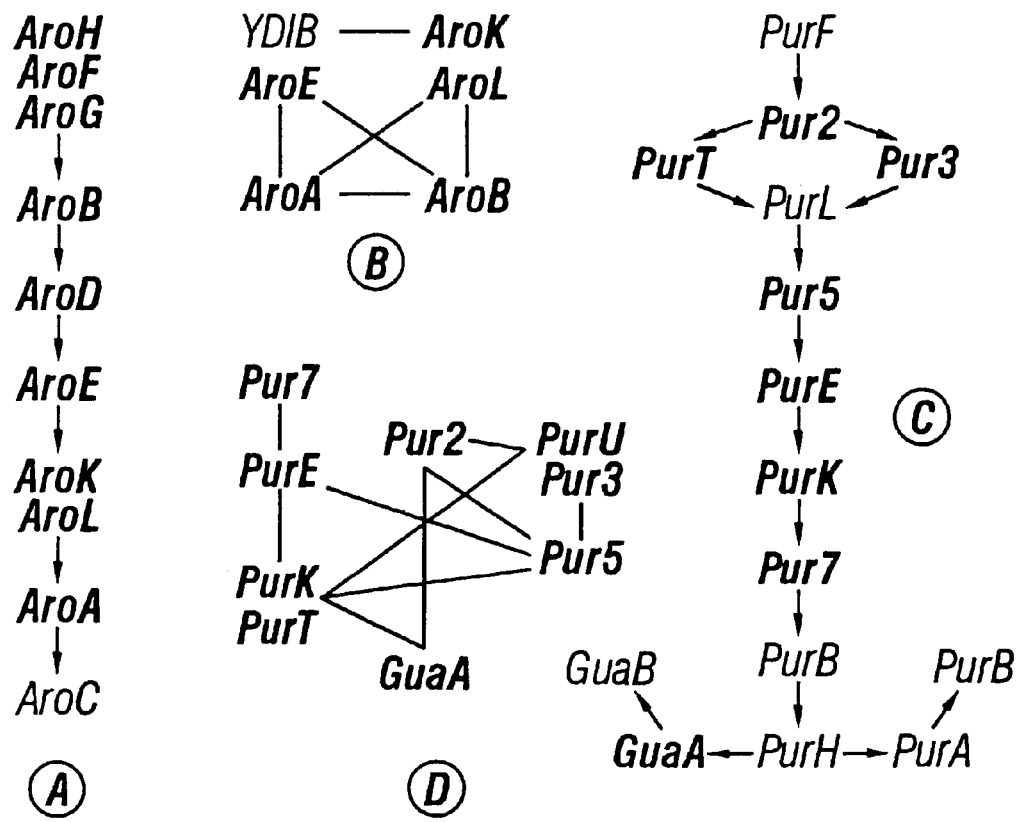
FIG. 5 shows suggestive information on pathways and complexes from linked pairs of proteins. 5A and 5C represent the shikimate biosynthesis pathway and purine synthesis pathway, respectively. 5B and 5D describe the links suggested by the Rosetta Stone method.

The recognition of many possible pair interactions between proteins of E. coli lead to the search for coupled interactions, where A is predicted to interact with B and B with C, and so forth. That is, a determination of whether the Rosetta Stone method can turn up complexes of proteins or protein pathways was examined. As FIG. 5 shows, suggestive information on both pathways and complexes did emerge from linked pairs of E. coli proteins. FIG. 5A represents the pathways for shikimate biosynthesis and FIG. 5C represents the pathway for purine biosynthesis. The enzymes in these pathways for which links were found to other members of the same pathway are shown in bold type. The precise links suggested by Rosetta Stone sequences are shown in panels FIGS. 5B and D. Some of these discovered links are between sequential enzymes in the pathway, and others are between mote distant members perhaps suggesting a multienzyme complex. An alternative explanation of the same findings is that enzymes in the pathway are expressed in a fused form in some organisms as an aid in regulation of expression; in this case linked members of a pair would not necessarily bind to each other (see below).

To evaluate the reliability of Rosetta Stone predictions of protein interactions, it is helpful to consider why the method should work in the first place. This emerges from considerations of protein affinity. It follows from the laws of thermodynamics that the fusion of protein domains A and B into a single protein chain can profoundly enhance the affinity of A for B. The reason for this is that fusion greatly reduces the entropy of dissociation of A with B, thereby reducing the association free energy of A to B. This reduction in entropy is often expressed as an increase in the effective concentration of A with respect to B. The concentrations of proteins in E. coli cells tend to be of the order of micromolar (Pederson et al. Cell 14,179(1978)) whereas the effective concentrations of fused proteins can be ~mM or even greater (Robinson et al. PNAS USA 95, 5929 (1998)). Put another way, the standard free energy of dissociation protein subunits from a complex is typically 8–20 kcal/mole at 27° C. (corresponding to dissociation constants of $10^{-6}$ to $10^{-14}$ M) (Horton and Lewis, Protein Sci. 1, 169 (1992)), and can be reduced by ~10 kcal/mol when the subunits are fused into a single protein chain. Because affinity between proteins A and B is greatly enhanced when A is fused to B, some interacting pairs of proteins may have evolved from primordial proteins that included the interacting domains A and B on the same polypeptide, as shown in FIG. 6.

Figure 6:
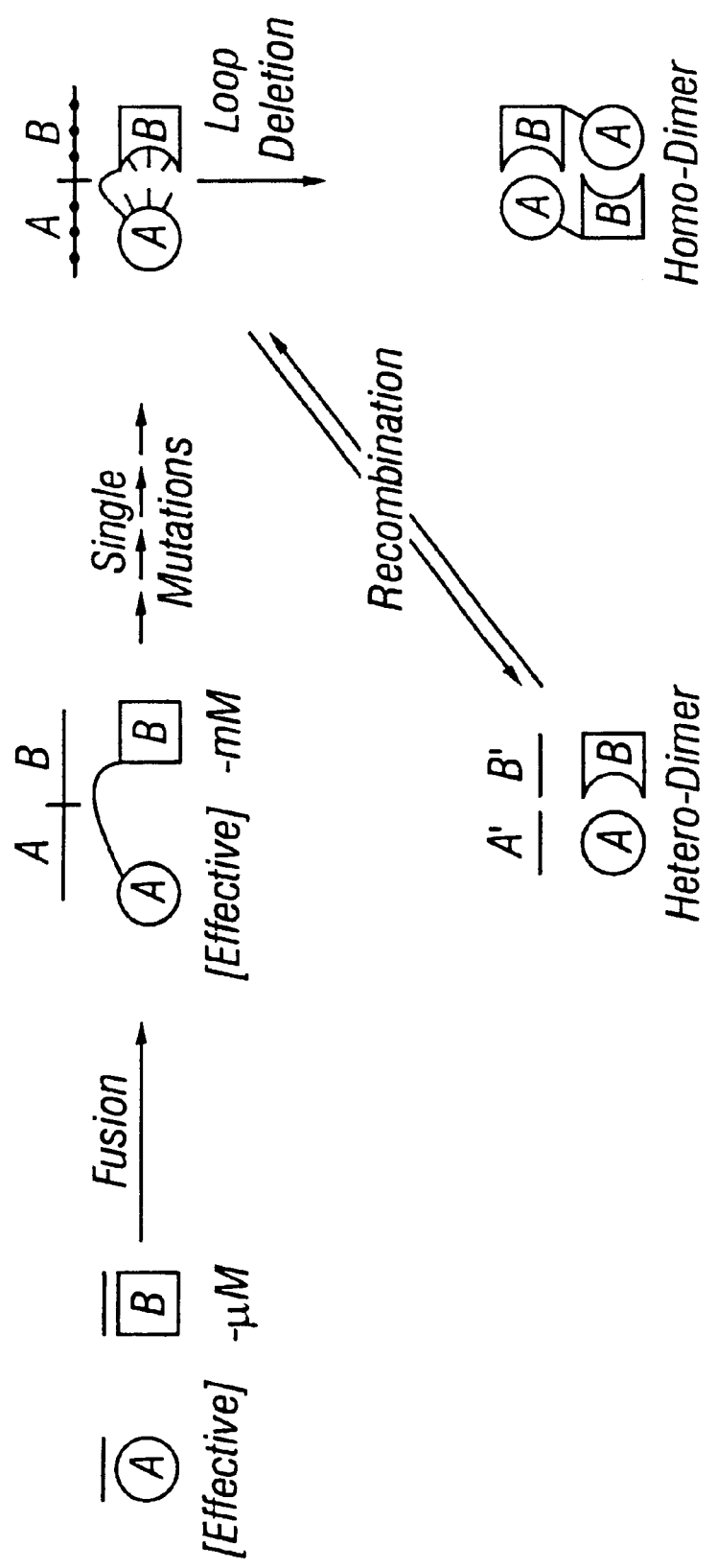
FIG. 6 shows a model for the evolution of protein-protein interactions. The Rosetta Stone model starts with the fusion of the genes that code for the non-interacting domains A and B, leading to expression of the fused two-domain protein AB.

FIG. 6 shows a model for the evolution of protein-protein interactions. The Rosetta Stone model starts with the fusion of the genes that code for the non-interacting domains A and B, leading to expression of the fused two-domain protein AB (see Table II of J. S. Richardson, Adv. Protein Chem., 34, 167 (1981). Note that eukaryotic genes, in contrast to prokaryotic genes, often code for multidomain proteins. In the fused protein, the domains have a relatively high effective concentration, and relatively few mutations create a primitive binding site between the domain that is optimized by successive mutations. In the second line, the interaction domains are separated by recombination with another gene to create an interacting pair of proteins A and B. An interacting pairs of proteins A and B can be created by fission of a protein, so that the preliminary fusion step is not essential to the Rosetta Stone hypothesis. The lower right-hand step shows another possible mutation, a loop deletion that leads to a domain-swapped homodimer. This evolutionary path to homooligomers is the analog for homooligomers of the evolutionary path suggested here for heterooligomers. This pathway is termed the Rosetta Stone hypothesis for evolution of protein interactions. Also in support of the Rosetta Stone pathway is the observation that protein-protein interfaces have strong similarity to interdomain' interfaces within single protein molecules (Tsai and Nussinov, J. Mol Biol. 260, 604 (1996)).

It is important to realize that the Rosetta Stone Method makes two distinct predictions. First it predicts protein pairs that have related biological function—that is, proteins that participate in a common structural complex, metabolic pathway, or biologic process. Prediction of function is robust: For $E.$ $coli$, general function similarity was observed in over half the testable predictions. Second, the method predicts potential protein-protein interaction. For this more specific prediction, the considerations of protein affinity and evolution aid understanding in which cases the Rosetta Stone method will miss pairs of interaction proteins (false negative) and in which cases it will turn up false candidates for interaction pairs (false positive). One reason for missing interaction is that many protein-proteins interactions may have evolved through other mechanisms, such as gradual accumulation of mutations to evolve a biding site. In these cases, there never was a fusion of the interaction proteins, so no Rosetta Stone protein can be found. Second, even in other cases when the interaction partners were once fused, the fused protein may have disappeared during the course of evolution, so there is no Rosetta Stone relic remaining to decipher binding partnerships. As more genomes are sequenced, however there is a higher chance of finding Rosetta Stone proteins.

False predictions of physical interactions may be made by the Rosetta Stone method in cases where domains are fused but not interacting. This may be so when proteins have been fused to regulate coexpression or protein signaling. For these cases, the "interaction" of the proteins can be functional interactions rather than physical interactions. Other false predictions can arise because the Rosetta Stone method cannot distinguish between homologs that bind, and those that do not. As an example, consider the signaling domains SH2 and SH3. The kinase domain and the SH2 and SH3 domains of the src homology kinase interact with one another in the src molecule (Xu et al. Nature 385, 595 (1997); Sicheri et al. Nature 385, 602 (1997)), but homologs of these domains are found in many other proteins, and it is certainly untrue that all SH2 domains interact with all SH3 domains. A similar problem crops up with EGF and immunoglobulin domains. That is, although the Rosetta Stone method gives a robust prediction of protein function of the form "A is functionally linked to B," only a subset of these putative interactions represent physical interactions between proteins.

To quantify and reduce errors in predicting protein-protein interactions the occurrence of "promiscuous" domains such as SH3 that are present in many otherwise different proteins are calculated. These domains can be identified and removed during domain fusion analysis (i.e., The Rosetta Stone Method). In the ProDom database of domains, the number of other domains that each domain could be linked to using the Rosetta Stone method were counted.

Figure 7:
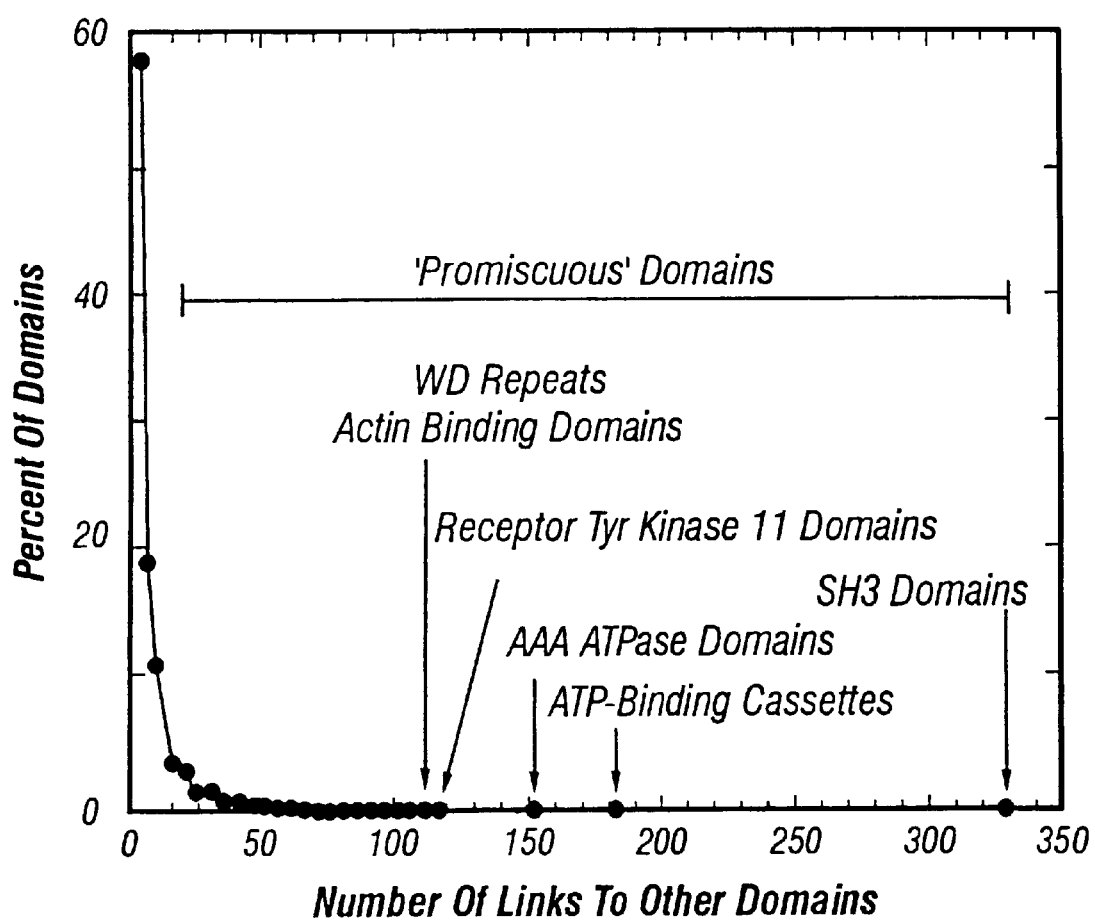
FIG. 7 depicts the occurrence of promiscuous protein domains, those that are found in many different proteins and are therefore linked to many different domains.

As shown in FIG. 7, about 95% of the domains are linked to only a few other domains. For the 7872 domains in the ProDom domain database for which we can find Rosetta Stone links, only about 5% are "promiscuous," making more than 25 links to other domains. By filtering only 5% of all domains from our Rosetta Stone method, one can remove the majority of falsely predicted interactions. When this type of filtering is applied to the 3531 Rosetta Stone links of $E.$ $coli$ found with the ProDom analysis, the number is reduced to 749. Although dropping the number of predictions, this filtration step increase the likelihood that predicted links represent true physical interactions by 47% over the unfiltered predictions. Accordingly, the identification in a genome of many pairs of protein sequences A' and B' that are both homologs to a single sequence AB in another genome suggests the possibility that A' and B' are binding partners and provides functional information about A' and B'.

Phylogenetic Profile Method

We computed phylogenetic profiles for the 4290 proteins encoded by the genome of $E.$ $coli$ by aligning each protein sequence, $P_i$, with the proteins from 16 other fully sequenced genomes (listed at the web site of The Institute for Genome Research) using the BLAST algorithm. Proteins coded by the $n^{th}$ genome are defined as including a homolog of $P_i$ if one of them aligns to $P_i$ with a score that is deemed statistically significant.

Figure 8A:
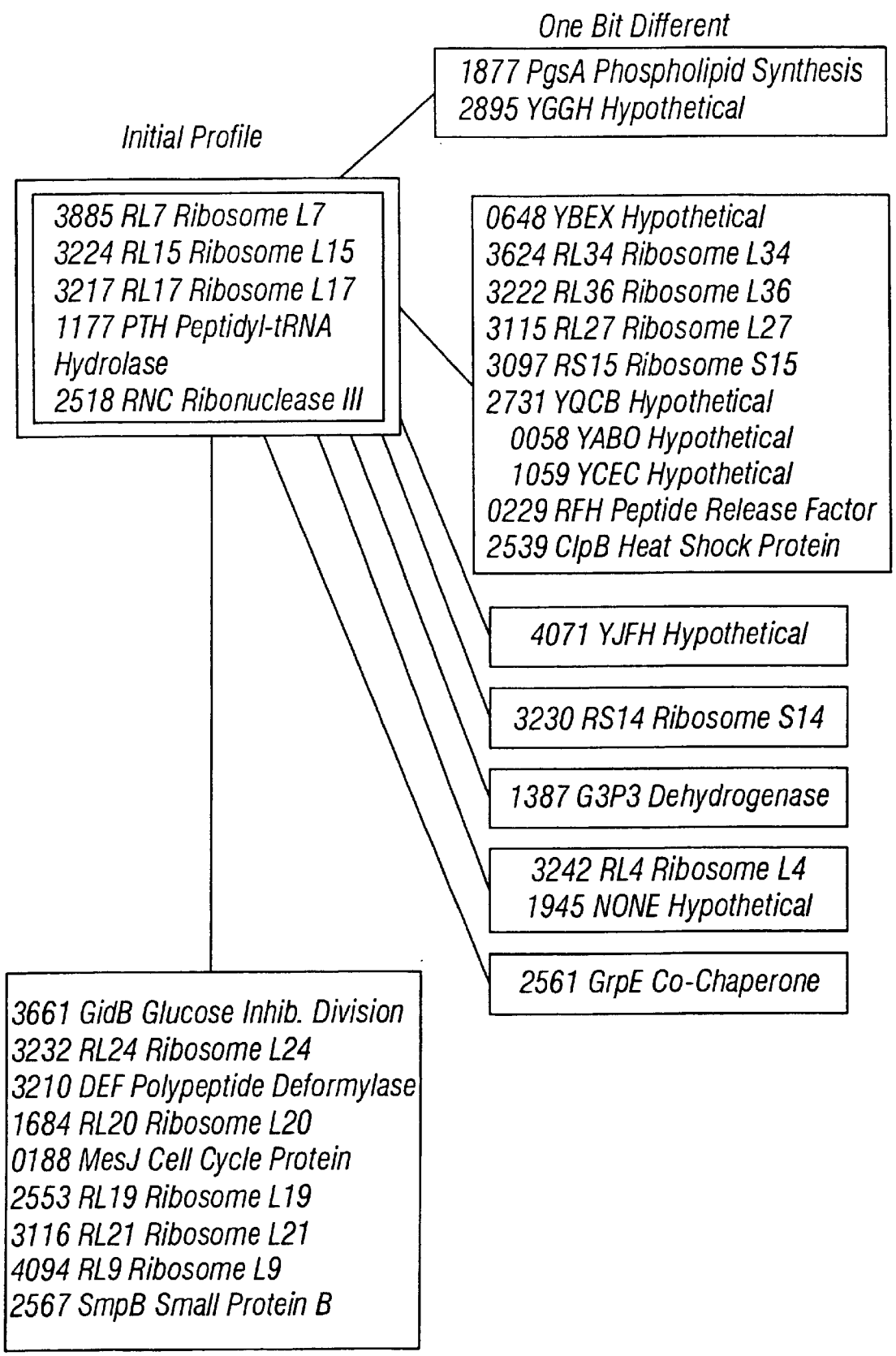
FIG. 8 is a diagram showing the process and result of the method of phylogenetic profiles. In each case all proteins with identical profiles to the query proteins were found (within the double box) and then all those with profiles that differed by one bit (in the second column). Proteins in bold face participate in the same complex or pathway as the query protein and in italics participate in a different but related complex or pathway. Proteins with identical profiles are shown within a box. Single lines between boxes represent a one-bit difference between the two profiles. All neighboring proteins whose profiles differ by one bit from the query protein are shown. Homologous proteins are connected by a dashed line or indented. Each protein is labeled by a four-digit E. coli number, a Swissprot gene name and a brief description. Notice that proteins within a box or in boxes connected by a line have similar functions. Hypothetical proteins (i.e. of unknown function) are prime candidates for functional and structural studies. Proteins in the double boxes in (a), (b) and (c) have respectively 11, 6, and 10 ones in their phylogenetic profiles, out of a possible 16 for the 17 genomes available at the time of calculation.
Figure 8B:
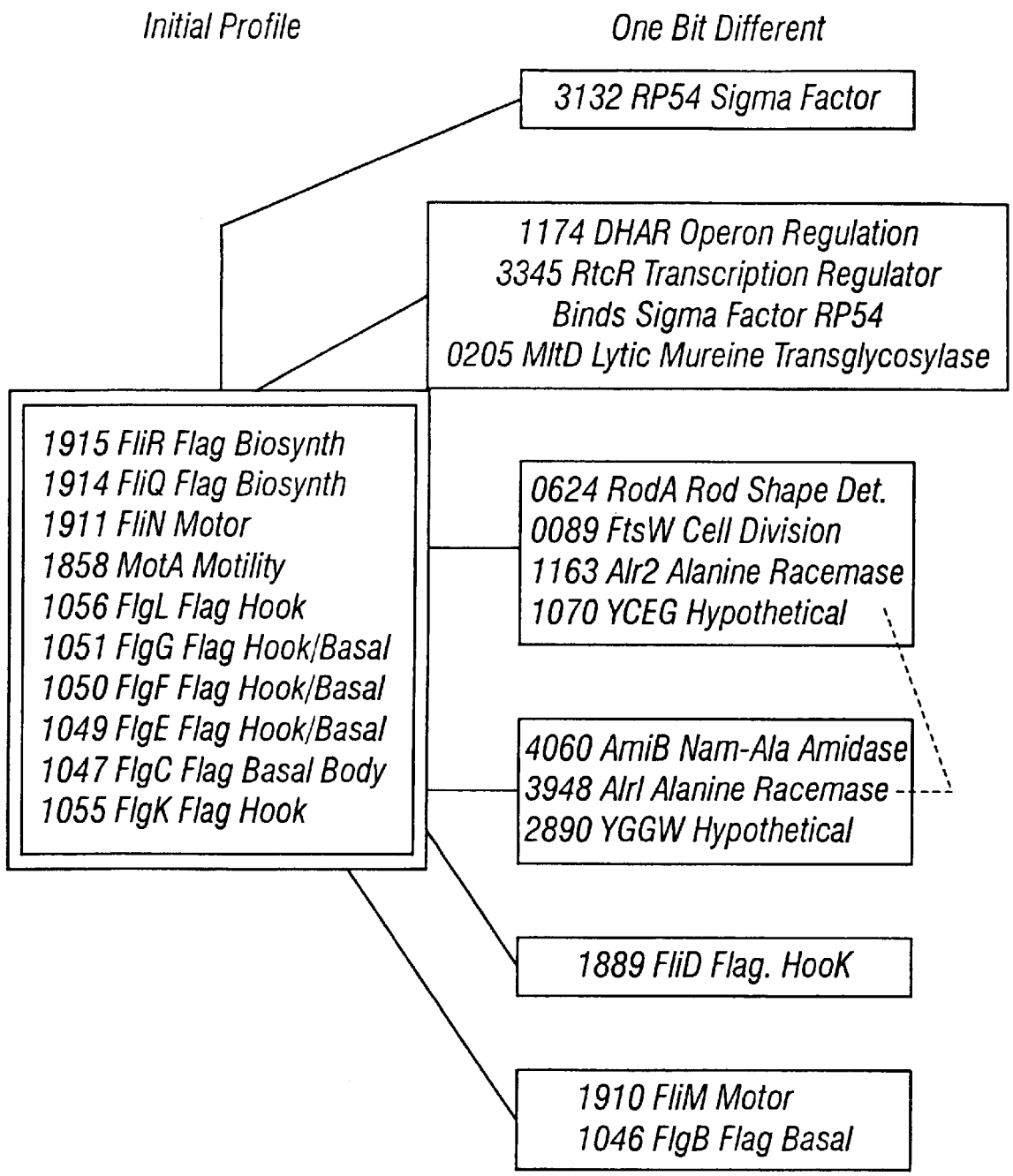
Figure 8C:
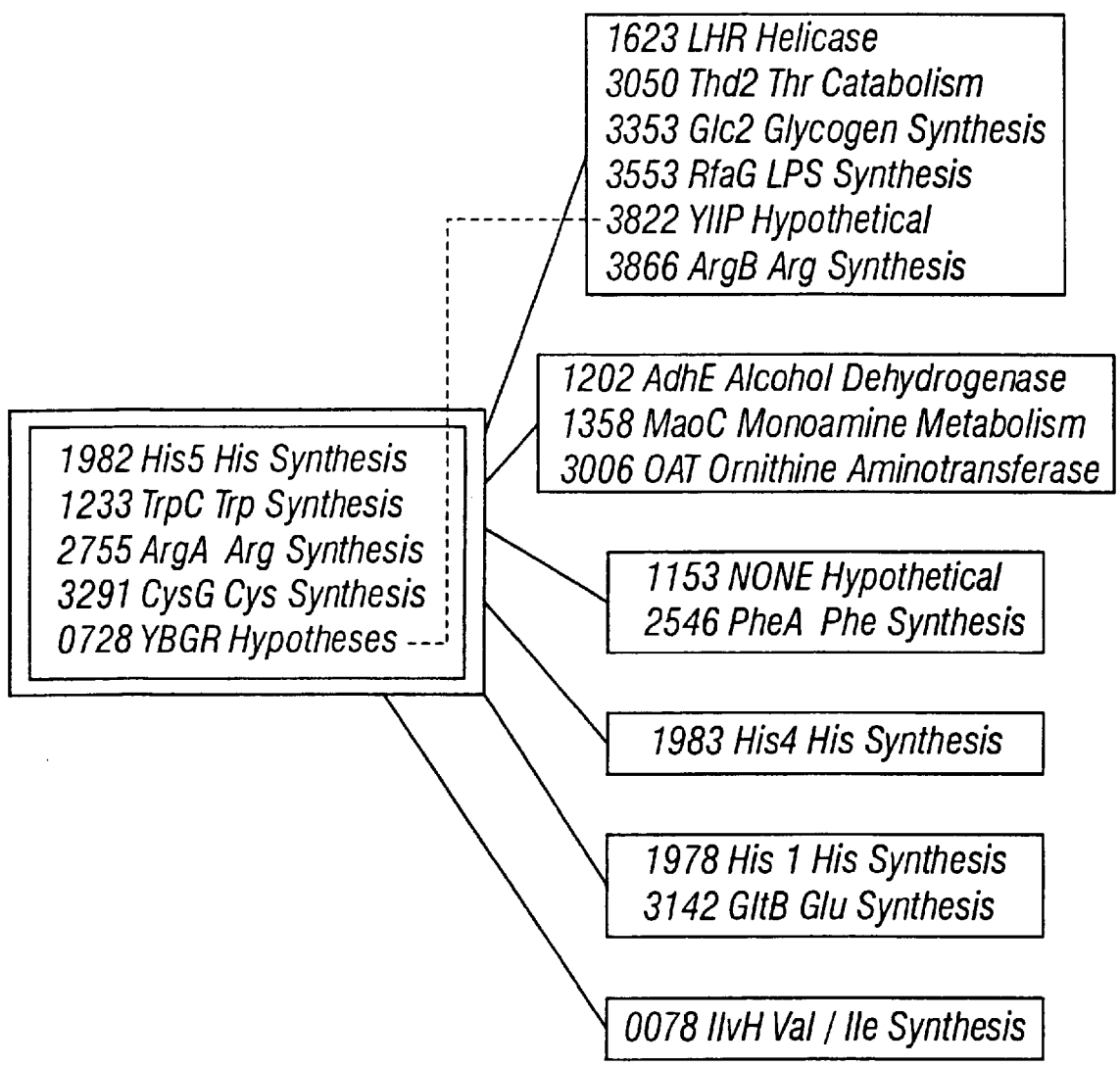

To test whether proteins with similar phylogenetic profiles are functionally linked, the phylogenetic profiles for two proteins that are known to participate in structural complexes, the RL7 ribosome protein and the FlgL flagellar structural protein, and one known to participate in a metabolic pathway, the HIS5 histidine biosynthetic protein were examined. As a first step all other $E.$ $coli$ open reading frames with identical phylogenetic profiles and then those with profiles that differ by one bit were identified. The results are shown in FIG. 8($a$) RL7; ($b$) FlgL; and ($c$) HIS5. Homologs of ribosome protein RL7 are found in 10 of 11 eubacterial genomes, as well as in yeast, but not in archaeal genomes. In FIG. 8($a$) we find that more than half of the $E.$ $coli$ proteins with the RL7 phylogenetic profile, or profiles that differ by one bit, have functions associated with the ribosome. Since none of these proteins has significant amino acid sequence similarity to RL7, the functional relationships to the ribosome, had they not been known already, could not be inferred by sequence comparisons. This finding supports the idea that proteins with similar profiles are likely to belong to a common group of functionally linked proteins. Several other proteins with these profiles have no assigned function and are accordingly listed as hypothetical. The testable prediction of the clustering of phylogenetic profiles is that these as yet uncharacterized proteins have functions associated with the ribosome.

The comparisons of the phylogenetic profiles of flagellar proteins, reported in FIG. 8($b$), further support the idea that proteins with similar profiles are likely to be functionally linked. Ten flagellar proteins share a common profile. Their homologs are found in a subset of five bacterial genomes: *Aquifex aeolicus, Borrelia burgdorferi, Bacillus subtilis, Helicobacter pylori, Mycobacterium tuberculosis.* Other proteins that appear in neighboring clusters (groups of proteins that share a common profile) include various flagellar proteins and cell wall maintenance proteins. Flagellar and cell wall maintenance proteins may be biochemically linked, since flagella are inserted through the cell wall. For example, the lytic murein transglycosylase (MltD) has a phylogenetic profile that differs by only one bit from that of the FlgL flagellar structural protein. This transglycosylase cuts the cell wall for unknown reasons. Therefore another prediction is that this enzyme may participate in flagellar assembly.

While FIGS. 8($a$) and ($b$) include proteins in structural complexes, FIG. 8($c$) shows proteins involved in amino acid metabolism. It was found that more than half the proteins with phylogenetic profiles similar (within one bit) to that of the His5 histidine synthesis protein are involved in amino acid metabolism.

The examples of FIG. 8 show that proteins with similar phylogenetic profiles to a query protein are likely to be functionally linked with it. The converse shows that groups of proteins known to be functionally linked often have similar phylogenetic profiles. In Table I groups of E. coli proteins were chosen that share a common keyword in their Swissprot annotation, reflecting well known families of functionally linked proteins. Since homologous proteins coded by the same genome necessarily have similar profiles, they were eliminated from the groups. For each group, the number of protein pairs that are "neighbors" were computed, where neighbors are defined as proteins whose profiles differ by less than 3 bits. For a group of N proteins there are at most $(N(N-1))/2$ possible neighbors.

TABLE I

Phylogenetic profiles link proteins with similar keywords

| Keyword | Number of Proteins* | Number of neighbors in Keyword group† | Number of neighbors in random group‡ |
|---|---|---|---|
| Ribosome | 60 | 197 | 27 |
| Transcription | 36 | 173 | 10 |
| tRNA synthase & ligase | 26 | 11 | 5 |
| Membrane proteins | 25 | 89 | 5 |
| Flagellar | 21 | 81 | 3 |
| Iron & Ferric & Ferritin | 19 | 16 | 3 |
| Galactose metabolism | 18 | 31 | 2 |
| Molybdate & Molybdenum & Molybdoterin | 12 | 6 | 1 |
| Hypothetical | 1084 | 108226 | 8440 |

*E. coli proteins grouped on the basis of a common keyword extracted from their annotation in the Swissprot database.
†Number of protein pairs, $N_{kw}$, in the keyword group with profiles that differ by less than 3 bits. These pairs are termed neighbors.
‡Number of neighbors found on average for a random group of proteins of the same size as the keyword group. Only membrane proteins without uniformly zero phylogenetic profiles were included.

Proteins grouped on the basis of similar keywords in Swissprot have more similar phylogenetic profiles than random proteins. Column 2 gives the number of non-homologous proteins in the keyword group. Column 3 gives the number of protein pairs in the keyword group with profiles that differ by less than 3 bits. These pairs are termed neighbors. Column 4 lists the number of neighbors found on average for a random group of proteins of the same size as the keyword group. Only membrane proteins without uniformly zero phylogenetic profiles were included. Unlike the other rows of the table, the hypothetical proteins do contain homologous pairs.

The similarity of the phylogenetic profiles of the proteins that share a common keyword is evaluated by a statistical test: the number of neighbors found in our keyword groups were compared to the average number of neighbors found in a group of the same size but with randomly selected E. coli proteins. We find that the random sets contain on average very few neighbors compared to the keyword groups, even though the keyword groups contain only a fraction of all possible neighbor pairs. Thus proteins that are functionally linked are far more likely to be neighbors in profile space than randomly selected proteins. However, only a fraction of all possible neighbors within a group were found. Therefore not all functionally linked proteins have similar profiles; they may fall into multiple clusters in profile space. It is interesting to note that hypothetical proteins are also more likely to be neighbors than random proteins, suggesting that many hypothetical proteins are part of uncharacterized pathways or complexes.

A second indication that functionally linked proteins are likely to have similar phylogenetic profiles comes from the analysis of classes of proteins obtained from the EcoCyc library (Encyclopedia of E. coli genes and metabolism). Several classes that contain more than ten members and represent well known biochemical pathways were selected. These results are listed in Table II. The results indicate that this analysis is similar to those found with the keyword groups: members of the group are far more likely to have neighboring profiles than a randomly selected control group.

TABLE II

Phylogenetic profiles link proteins in EcoCyc classes

| EcoCyc Class | Number of proteins* | Number of neighbors in EcoCyc Class† | Number of neighbors random group‡ |
|---|---|---|---|
| Carbon compounds | 88 | 798 | 60 |
| Anaerobic respiration | 66 | 275 | 30 |
| Aerobic respiration | 28 | 39 | 6 |
| Electron transport | 26 | 91 | 5 |
| Purine biosynthesis | 21 | 11 | 3 |
| Salvage nucleosides | 15 | 10 | 1 |
| Fermentation | 19 | 17 | 3 |
| TCA cycle | 16 | 6 | 1 |
| Glycolysis | 14 | 5 | 1 |
| Peptidoglycan biosynthesis | 12 | 10 | 1 |

*E. coli proteins grouped according to metabolic function on the basis of EcoCyc (Encyclopedia of E. coli genes and metabolism) classes.
†The number of protein pairs, $N_{EC}$, in the EcoCyc class with profiles that differ by less than 3 bits. These pairs are termed neighbors.
‡Number of neighbors found on average for a random group of proteins of the same size as the keyword group.

Proteins grouped according to metabolic function on the basis of EcoCyc classes have more similar phylogenetic profiles than random proteins. Column 2 gives the number of proteins in the EcoCyc class. Column 3 gives the number of protein pairs in the EcoCyc class with profiles that differ by less than 3 bits. These pairs are termed neighbors. Column 4 lists the number of neighbors found on average for a random group of proteins of the same size as the keyword group.

The ability of the method to predict the function of uncharacterized proteins was tested. The function of a protein with that of its neighbors in phylogenetic profile space was equated. This is accomplished by means of the keyword annotations found within the Swissprot database. To test how effective this method is the keywords of each characterized protein were compared to those of the neighbors in phylogenetic profile space. The neighbors, in this case, were all other proteins with an identical profile or were proteins with a vector distance profile whose Euclidean distance was within 2 evolutionary units. It was found that on average 43% of the neighbor keywords overlapped the known keywords of the query protein. By comparison, random proteins had only a 4% overlap with the same set of neighbors. Thus, a rough estimate was made that for more than half of E. coli proteins one can correctly assign the general function by examining the functions of their phylogenetic profile neighbors. This estimate should also hold for the ability of phylogenetic profiles to assign functions to uncharacterized proteins.

As another example, the phylogenetic profiles for the 6217 proteins encoded by the genome of the yeast Saccharomyces cerevisiae, employing the same methods used for E.

coli proteins were computed. As in *E. coli*, where function of a protein was already known, one could test the predicted function. In yeast, it was found that on average 29% of the neighbor keywords overlapped the known keywords of the query protein, compared to 8% overlap for random proteins.

The phylogenetic profile of a protein describes the presence or absence of homologs in organisms. Proteins that make up multimeric structural complexes are likely to have similar profiles. Also, proteins that are known to participate in a given biochemical pathway are likely to be neighbors in the space of phylogenetic profiles. This demonstrates that comparing profiles is a useful tool for identifying the complex or pathway that a protein participates in. The method of the invention is able to make functional assignments of uncharacterized proteins by examining the function of proteins with identical phylogenetic profiles.

As the number of fully sequenced genomes increases, scientists will be able to construct longer, and potentially more informative, protein phylogenetic profiles. There are at least 100 genome projects underway due for completion within the next few months. These data will allow construction of profiles of length 100 rather than 16 bits. Because the number of profile patterns grows exponentially with the number of fully sequenced genomes, the results of 50 bit comparisons should be considerably more informative than those with 16 bits. Furthermore, because the newly sequenced genomes will include several eukaryotic organisms, protein phylogenetic profiles should also become a useful tool for studying structural complexes and metabolic pathways in these higher organisms.

Combination Methods

As discussed above, phylogenetic profiles allow sequence unrelated, but functionally-related, proteins to be grouped together. A similar analysis can be performed by considering the constraint that proteins that function together are usually present in the cell at the same time. Such a method exploits the synchronous protein expression requirement by analyzing mRNA expression patterns in yeast grown under a variety of conditions. In practice proteins with similar mRNA expression patterns are grouped and show that they often have similar functions. (see Eisen et al., *Proc. Natl. Acad. Sci. USA* 95, 14863–8 (1998)). In much the same way, proteins could be clustered according to spatial expression patterns by analyzing tissue- or cellular compartment-specific expression patterns. In addition, the Rosetta Stone method can be used to predict functional interactions between different proteins in one organism by virtue of their fusion into a single protein in another organism. Combining these three independent methods of prediction with available experimental data is presented here to demonstrate the first large-scale prediction or protein function. These methods established links between proteins of closely related function in the yeast *Saccharmyces cerevisiae*.

Experimental Interactions. Pairwise links were created between yeast proteins known from experimental literature to interact by such techniques as co-immunoprecipitation and yeast two-hybrid methods. We combined interaction data from the MIPS database and the Database of Interacting Proteins, a community-developed database of protein-protein interactions.

Linking of Metabolic Pathway Neighbors. Yeast homologs in *E. coli* proteins were found by BLAST homology searches. Pairwise links were defined between yeast proteins whose *E coli* homologs catalyze sequential reactions (or one reaction step further away) in metabolic pathways, as defined in the EcoCyc database.

Calculation of Correlated Evolution. Phylogenetic profiles were constructed for each yeast protein as described above:

Calculation of Correlated mRNA Expression. Results of 97 individual publicly-available DNA chip yeast mRNA expression data sets were encoded as a string of 97 numbers associated with each yeast open reading frame (ORF) that described how the mRNA containing that open reading frame changed levels during normal growth, glucose starvation, sporulation, and expression of mutant genes. This string is the analogue within one organism of a phylogenetic profile. The mRNA levels for each of the 97 experiments were normalized, and only genes that showed a 2 standard deviation change from the mean in at least one experiment were accepted, thereby ignoring genes that showed no change in expression levels for any experiment. ORF's with correlated expression patterns were, grouped together by calculating the 97-dimensional Euclidian distance that describes the similarity in mRNA expression patterns. ORFS were considered linked if they were among the 10 closest neighbors within a given distance cutoff, conditions that maximized the overlap of ORF annotation between neighbors.

Calculation of Correlated Gene Fusion Events. Proteins were linked by Rosetta Stone patterns as described above as well as by calculating what could be called incomplete triangle relationships between proteins. Alignments were found with the program Psi-Blast.

Figure 9:
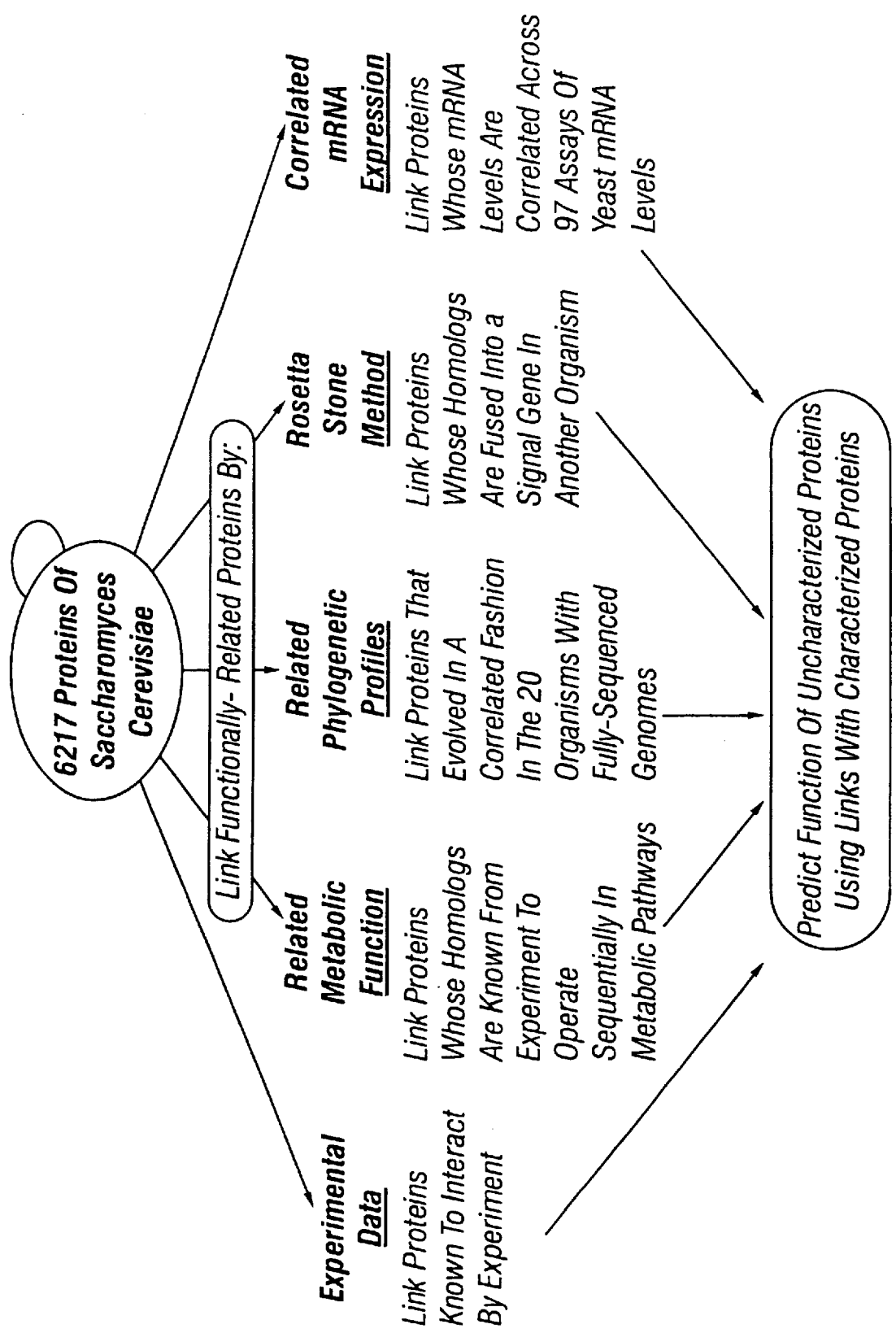
FIG. 9 shows strategies used to link functionally-related yeast proteins as described in the Examples.

An analysis using these methods identified 20,749 protein-protein links from correlated phylogenetic profiles, 26,013 links from correlated mRNA expression patterns, and 45,502 links from Rosetta Stone sequences. As shown in FIG. 9, these links were combined with an additional 500 experimentally-derived protein-protein interactions from the Database of Interacting Proteins and the MIPS yeast genome database (Mewes et al. Nucleic Acids Res. 26, 33–37 (1998)), and 2,391 links among yeast proteins that catalyze sequential reactions in metabolic pathways.

Of the 3,750 total functional links found among 4,701 (77%) of the yeast proteins, 4,130 were defined to be of the 'highest confidence' (known to be correct by experimental techniques or validated by 2 of the 3 prediction techniques); 19,521 others are defined as 'high confidence' (predicted by phylogenetic profiles), and the remainder were predicted by either correlated gene fusion or correlated mRNA expression, but not both.

The quality of the links was evaluated as follows: one assumes that if one links a protein, A', to a group of functionally-related proteins, the shared functions of these other proteins provide a clue to the general function for A'. Where the function of A' is already known, one can test the predicted function. For this test the standardized keyword annotation of the Swiss-Prot database was chosen and used to systematically compare the known function of all characterized yeast proteins to the function predicted by the methods of the invention. As one example chosen from the many yeast proteins tested, the Swiss-Prot keywords for the enzyme ADE1, which catalyzes the seventh step of de novo purine biosynthesis, are "Purine Biosynthesis" and "ligase". Based upon the frequencies with which keywords appear in the annotation of proteins linked to ADE1, it is predicted that the general function of ADE1 to be Purine biosynthesis (13.6%), Transferase (11.4%), Ligase (6.8%), and Lyase (13.6%). Therefore, the analysis is used to predict the general biological process that a protein, here ADE1, participates in, as well as to link the protein to many other proteins of closely related function. The results of the systematic keyword analyses are listed in Table III, along with confidence levels, data coverage, and comparisons to random trials. The links verified by two independent prediction techniques predict protein function with the same reliability as experimental interaction data and at over eight times the level of random trials.

TABLE III

Prediction of function of yeast proteins: data coverage and reliability of predictions

|  | # of proteins | # of Functional Links | Ability to Predict Known Function* | Ability in Random Trials† | Signal to Noise‡ |
|---|---|---|---|---|---|
| Individual Prediction Techniques | | | | | |
| Experimental§ | 484 | 500 | 33.2% | 4.0% | 8.3 x |
| Metabolic pathway neighbors | 188 | 2,391 | 20.3% | 4.5% | 4.5 x |
| Phylogenetic profiles | 1,976 | 20,749 | 33.1% | 7.4% | 4.5 x |
| Rosetta stone method | 1,898 | 45,502 | 26.5% | 7.7% | 3.4 x |
| Correlated mRNA expression | 3,387 | 26,013 | 11.5% | 6.9% | 1.7 x |
| Combined Predictions | | | | | |
| Links made by ≧2 prediction techniques | 683 | 1,249 | 55.6% | 6.9% | 8.1 x |
| Highest Confidence Links | 1,223 | 4,130 | 40.9% | 5.5% | 7.4 x |
| High Confidence Links | 1,930 | 19,521 | 30.8% | 7.4% | 4.2 x |
| High and Highest Confidence Links | 2,356 | 23,651 | 32.0% | 6.8% | 4.7 x |
| All Links | 4,701 | 93,750 | 20.7% | 7.2% | 2.9 x |

*The predictive power of individual techniques and combinations of techniques was evaluated by automated comparison of annotation keywords. By the methods listed, each protein is linked to one or more neighbor proteins. For characterized proteins ("query" proteins), the mean recovery of known Swiss-Prot keyword annotation by the keyword annotation of linked neighbors was calculated as:

$$<\text{keyword recovery}> = \frac{1}{A}\sum_{i=1}^{A}\sum_{j=1}^{x}\frac{n_j}{N}$$

where A is the number of annotated proteins, x is the number of query protein Swiss-Prot keywords, N is the total number of neighbor protein Swiss-Prot keywords, and $n_j$ is the number of times query protein keyword j occurs in the neighbor protein annotation. Because functional annotations typically consist of multiple keywords, both specific and general, even truly related proteins show only a partial keyword overlap (e.g. approx. 35%).
†Mean recovery of Swiss-Prot keyword annotation for query proteins of known function by Swiss-Prot keyword annotation of randomly-chosen linked neighbors, calculated as in Equation (1) for the same number of links as exist for real links (averages of 10 trials).
‡Calculated as ratio of known function recovered by real links to that recovered by random links.
§Experimentally-observed yeast protein-protein interactions contained in the DIP and MIPS (Mewes et al. Nucleic Acids Res. 26:33–37 (1998)) databases.

These links provide a means to characterize proteins of unknown function. There are 2,557 uncharacterized proteins in yeast (Mewes et al. Nucleic Acids Res. 26:33–37 (1998)), proteins not studied experimentally and with no strong homologs of known function. Of these, 374, or 15%, can be assigned a general function from the high and highest confidence functional links and 1,524, or 60%, can be assigned a general function using all links.

Figure 10:
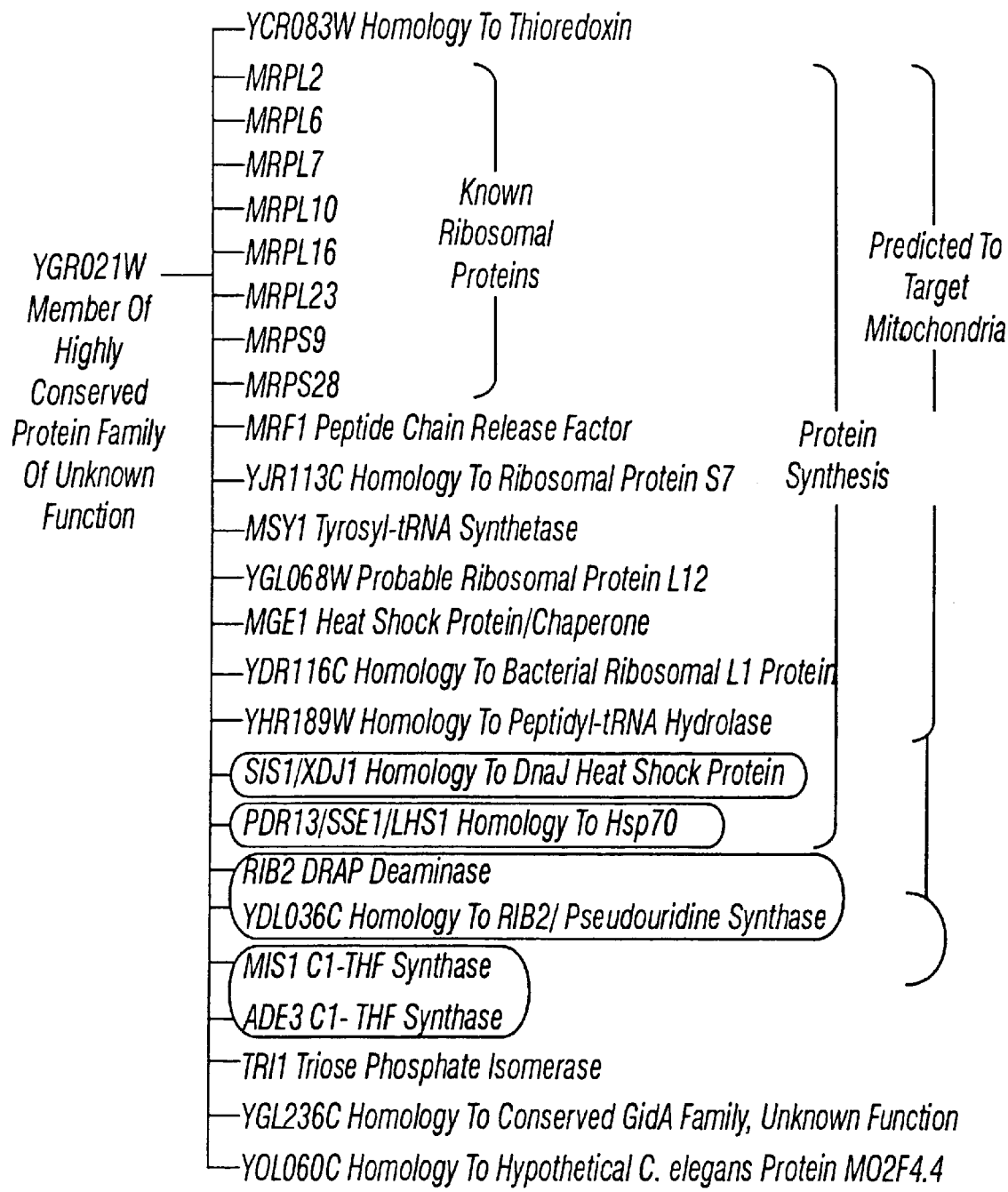
FIG. 10 shows the high confidence functional links found by phylogenetic profiles for the yeast protein YGR021 W, a member of a protein family conserved in many organisms but of entirely unknown function.

A specific example of the assignment of function is shown in FIG. 10 for a protein (yeast open reading frame YGR021W) from a highly conserved protein family of unknown function. On the basis of the methods described here and the functional links they uncover, this family can now be assigned a function related to mitochondrial proteins synthesis. Two of the functional partners of YGR021W are also proteins in conserved families of unknown function: the gidA family and the *C. elegans* M02F4.4 family. These families too can now be associated with mitochondrial (or bacterial) protein synthesis. The link to triose-phosphate isomerase (FIG. 10) is particularly interesting in light of the human myopathy in which a deficiency of this enzyme is correlated with grossly altered mitochondrial structure (Bardosi et al. *Acta Neuropathol* (Berl) 79, 387–394 (1990)).

Figure 11A:
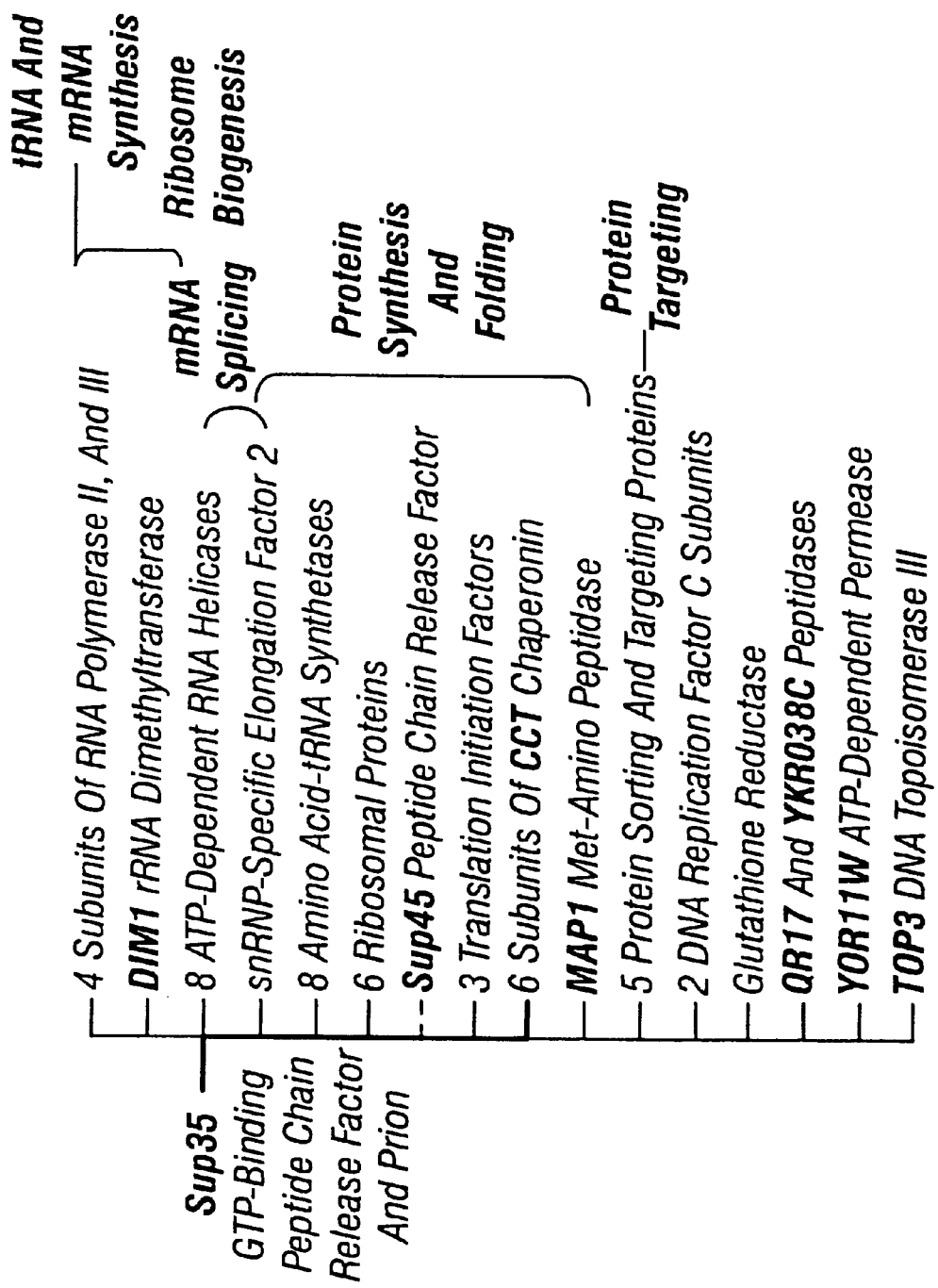
FIG. 11A shows high and highest confidence functional links established for the yeast prion Sup35. (11B) An illustration of the network of high (thin lines) and highest (bold lines) confidence links discovered among the proteins (open circles) linked to Sup35 (dark circle). The network of links shows a high degree of local clustering.
Figure 11B:
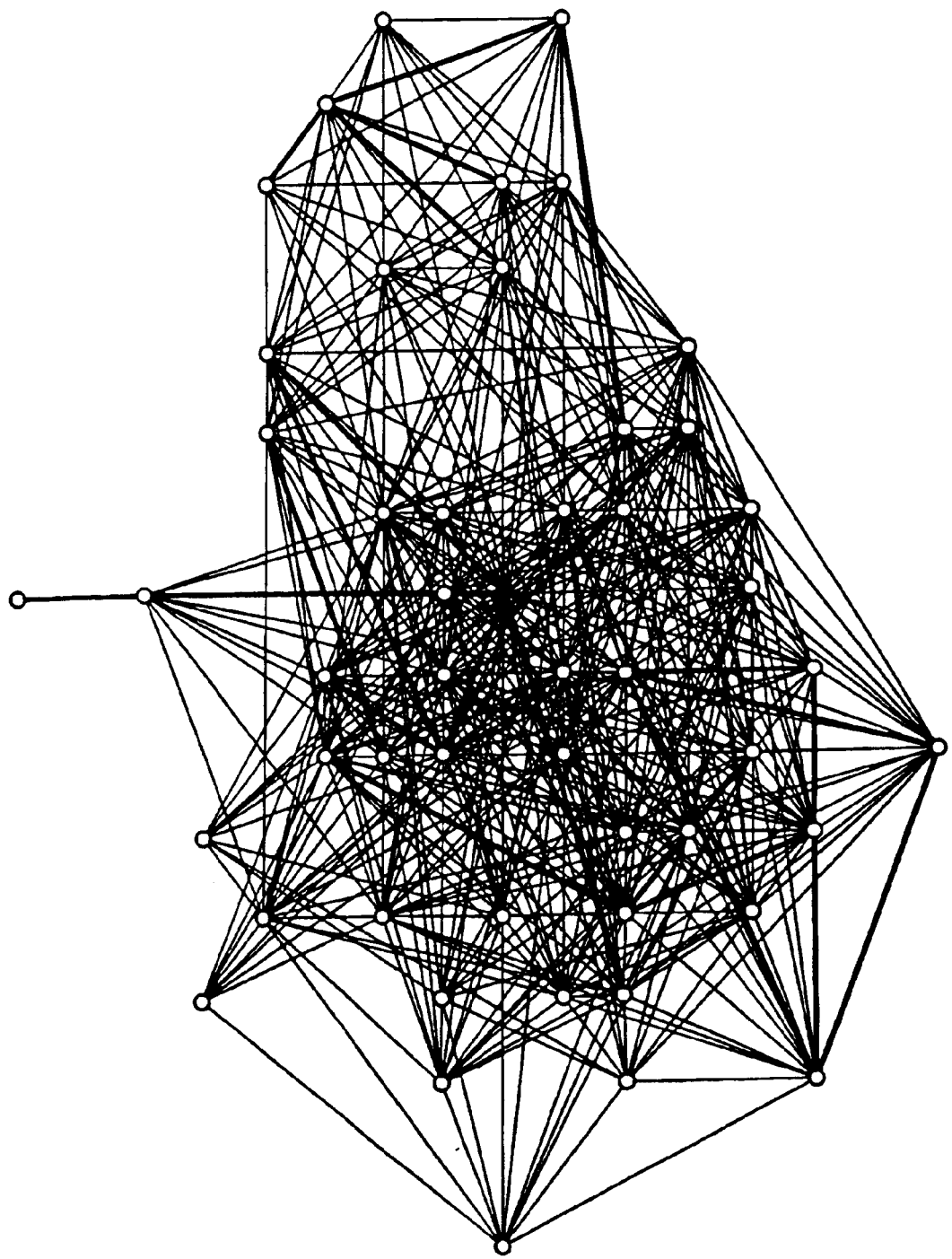

Two additional examples of links are given: those to the yeast prion Sup35 (Wickner, R. B., Science 264, 566–569 (1994)), and those to MSH6, the yeast homolog of human colon-cancer related genes (Miyaki et al., Nature Struct. Biol., 17, 271–272 (1997)). In both cases, a general function is already known, but the method of the invention also predicts novel functional links. In particular, in FIG. 11, the yeast prion Sup35, which acts as a translation release factor in its non-prion state, is linked with many proteins involved in protein synthesis consistent with Sup35's primary role of interacting with the ribosome to release the newly synthesized peptide chain (Kushirov et al., Gene 66, 45–54 (1988); Stansfield et al. EMBO J. 14, 4365–4373 (1995)). Also linked to Sup35 are protein sorting and targeting proteins, consistent with an accessory role in guiding nascent proteins to their final cellular destinations. Sup35 shows both correlated evolution and correlated mRNA expression with components of the CCT chaperonin system, a yeast chaperonin system believed to aid folding of newly synthesized actin and microtubules.

Novel links are also established when we examine MSH6, a DNA mismatch repair protein (Johnson et al., J. Biol.

Figure 12:
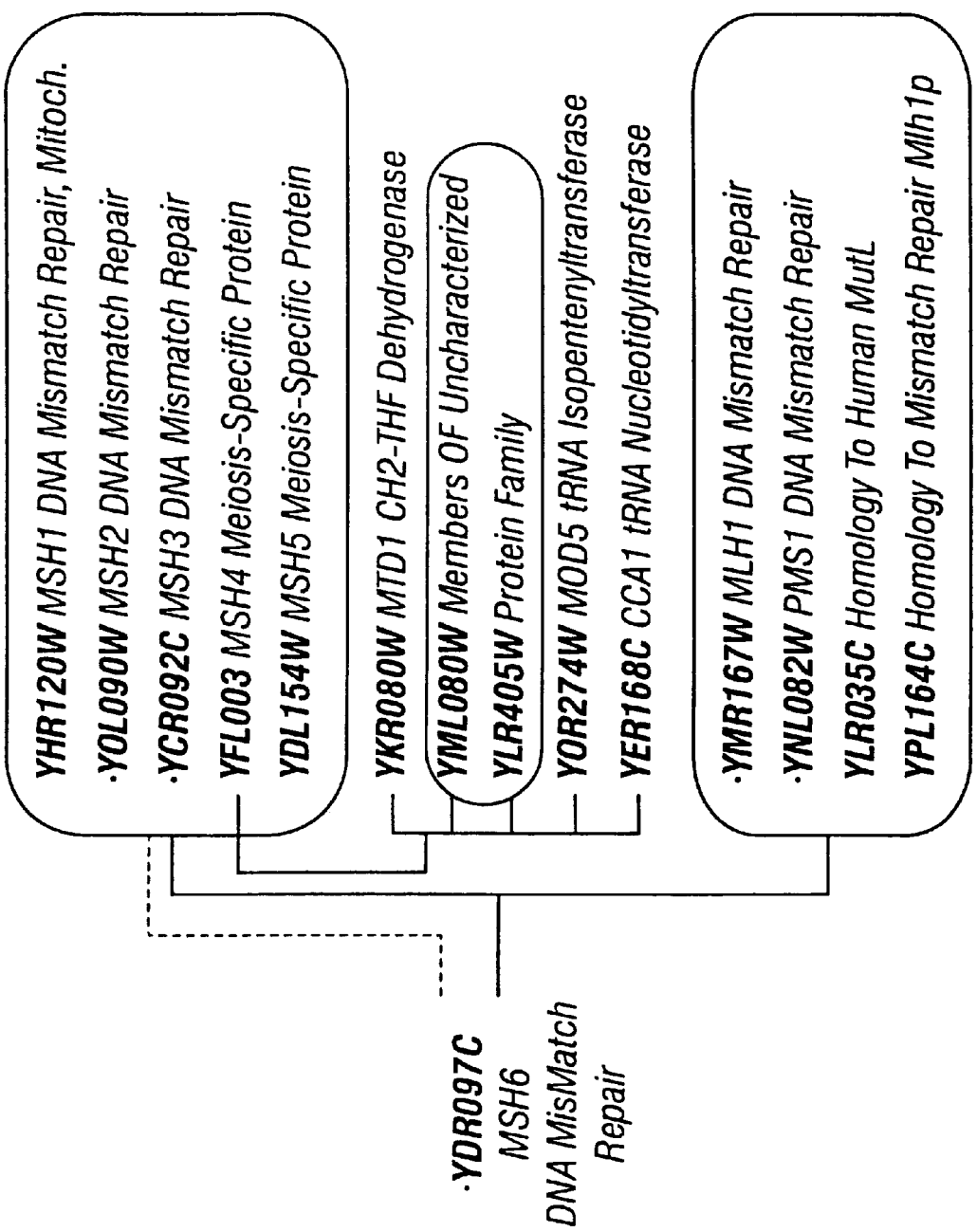
FIG. 12 shows high and highest confidence functional links found for the yeast DNA repair protein MSH6, which is similar in sequence to colorectal cancer-causing proteins in humans.

Chem. 271, 7285–7288 (1996)) whose human homologs, when mutated, cause the majority of hereditary nonpolypoid colorectal cancers (reviewed in: Lynch et al. Ann. N. Y. Acad. Sci., 833, 1–28 (1997)). MSH6 is homologous to several other DNA mismatch repair proteins and, in FIG. 12, is linked to the sequence-unrelated PMS1 DNA mismatch repair protein family, mutations of which, in humans, are also tied to colorectal cancer (Papadopolous et al., Science 263, 1625–1629 (1994)). MSH6 is in turn linked via homolog MSH4 to the purine biosynthetic pathway by methylenetetrhydrofolate dehydrogenase and, to two RNA modification enzymes, and, to an uncharacterized protein family, which can now be investigated in light of DNA repair and potential participation of human homologs in cancer.

A number of embodiments of the invention have been described. Nevertheless, it will be understood that various modifications may be made without departing from the spirit and scope of the invention.

What is claimed is:

1. A method for identifying pairs of proteins in a genome as being functionally linked, comprising:
    (a) providing a first plurality of protein sequences comprising substantially all protein sequences encoded by a first genome, or, a plurality of nucleic acid sequences comprising substantially all protein-encoding nucleic acid sequences in a first genotne;
    (b) providing a second plurality of protein sequences comprising substantially all protein sequences encoded by one or more additional genomes, or, a second plurality of nucleic acid sequences comprising substantially all protein-encoding nucleic acid sequences of one or more additional genomes;
    (c) comparing each protein sequence or nucleic acid sequence in the first plurality of protein sequences or nucleic acid sequences respectively with substantially all the protein sequences or nucleic acid sequences of the second plurality of protein sequences or nucleic acid sequences to determine if the protein sequence or nucleic acid sequence in the first genome has a homolog in the one or more additional genomes based on the degree of similarity of the sequences being compared;
    (d) generating a phylogenetic profile for each protein of the first genome, wherein the phylogenetic profile is a vector or pattern whose elements indicate whether a homolog of the protein or protein encoding nucleic acid sequence of the first genome is present or absent in each of the one or more additional genomes of the second plurality of protein sequences or nucleic acid sequences; and
    (e) linking proteins of the first genome having similar phylogenetic profiles, wherein proteins with similar profiles are identified as being functionally linked.

2. The method of claim 1, wherein the sequences of step (a) or step (b), or, step (a) and step (b), are present in one or more databases.

3. The method of claim 1, wherein the sequences of step (a) or step (b), or, step (a) and step (b), are in the form of a nucleic acid and an amino acid sequence.

4. The method of claim 3, wherein a nucleic acid sequence is translated to an amino acid sequence.

5. The method of claim 1, wherein the comparing of sequences to determine homology in step (c) or generating a phylogenetic profile in step (d) is performed by an algorithm.

6. The method of claim 5, wherein the algorithm to determine homology in step (c) is selected from the group consisting of a Smith-Waterman algorithm, a Needleman-Wunsch algorithm, a BLAST algorithm, a FASTA algorithm, and a PSI-BLAST algorithm.

7. The method of claim 1, wherein the determination as to whether a protein sequence or a nucleic acid sequence of step (a) has a homolog in another genome is based on whether the statistical significance of the sequence similarity exceeds a probability (p) value threshold.

8. The method of claim 1, wherein the phylogenetic profile is in the form of a vector, matrix or phylogenetic tree.

9. The method of claim 1, further comprising using a computer program, wherein the computer program comprises instructions for obtaining data, comparing data to form a phylogenetic profile, and grouping data.

10. The met hod of claim 1, wherein at least one of the steps of the method is performed by a computer.

11. The method of claim 1, further comprising using a computer program, wherein the computer program comprises instructions for aligning protein sequences or nucleic acid sequences and determining an evolutionary distance between proteins based on the protein sequences.

12. The method of claim 1, wherein the phylogenetic profile is generated using an evolutionary distance method.

13. The method of claim 1, wherein the phylogenetic profile is generated in a continuous code that describes how similar the related sequences are in the different genomes.

14. The method of claim 1, wherein the phylogenetic profile is generated using a bit type profiling method.

15. The method of claim 1, wherein the phylogenetic profile is generated using an evolution probability process, wherein the process comprises
    (a) constructing a conditional probability matrix: p(aa→aa'), where aa and aa' are any amino acids, and the conditional probability matrix is constructed by converting an amino acid substitution matrix from a log odds matrix to a conditional probability matrix;
    (b) accounting for an observed alignment of the constructed conditional probability matrix by taking the product and the conditional probabilities for each aligned pair of amino acids during the alignment of the two protein sequences, represented by $$P(p) = \prod_n p(aa_n \to aa'_n);$$

and
    (c) determining an evolutionary distance a from powers equation:

$$p' = p^\alpha(aa \to aa' \to), \text{ maximizing for P.}$$

16. The method of claim 15, wherein the conditional probability matrix is defined by a Markov process with substitution rates over a fixed time interval.

17. The method of claim 15, wherein the conversion from an amino acid substitution log odds matrix to a conditional probability matrix is represented by:

$$P_\beta(i \to j) = P(j) 2^{[BLOSUM62 ij/2]},$$

where BLOSUM62 is an amino acid substitution log odds matrix, and P(i→j) is the probability that amino acid i is replaced by amino acid j through point mutations according to BLOSUM62 scores.

18. The method of claim 17, wherein Pj's are the abundances of amino acid j and are computed by solving a plurality of linear equations given by the normalization condition that $$\sum_i P_B(i \to j) = 1.$$

19. A method for identifying pairs of proteins in a genome as being functionally linked, comprising:
    (a) providing a first plurality of protein sequences comprising substantially all protein sequences encoded by a first genome, or, a plurality of nucleic acid sequences comprising substantially all protein-encoding nucleic acid sequences in a first genome;
    (b) providing a second plurality of protein sequences comprising substantially all protein sequences encoded by one or more additional genomes, or, a second plurality of nucleic acid sequences comprising substantially all protein-encoding nucleic acid sequences of one or more additional genomes;
    (c) comparing each protein sequence or nucleic acid sequence in the first plurality of protein sequences or nucleic acid sequences respectively with substantially all the protein sequences or nucleic acid sequences of the second plurality of protein sequences or nucleic acid sequences to determine if the protein sequence or nucleic acid sequence in the first genome has a homolog in the one or more additional genomes based on the degree of similarity of the sequences being compared;
    (d) generating a phylogenetic profile for each protein of the first genome, wherein the phylogenetic profile is a vector or pattern whose elements indicate whether a homolog of a protein or protein-encoding nucleic acid sequence of the first genome is present or absent in each of the one or more additional genomes of the second plurality of protein sequences or second plurality of nucleic acid sequences; and
    (e) linking proteins of the first genome having similar phylogenetic profiles, wherein proteins with similar profiles are identified as being functionally linked;
    wherein the determination as to whether a protein sequence or a nucleic acid sequence of step (a) has a homolog in another genome is based on whether the statistical significance of the sequence similarity exceeds a probability (p) value threshold, and the probability threshold is set with respect to the value 1/NM, based on the total number of sequence comparisons that are to be performed, wherein N is the number of proteins in the first organism's genome and M in all other genomes.

20. A computer program, stored on a computer-readable medium, for identifying multiple polypeptides as having a functional link, the computer program comprising instructions for causing a computer system to:
    (a) obtain data comprising a list of protein sequences from at least two genomes;
    (b) compare the data to form a protein phylogenetic profile for each protein, wherein the protein phylogenetic profile indicates the presence or absence of a protein belonging to a particular protein family in each of the at least two genomes based on homology of the proteins, and determining the significance of the homology of the proteins by computing a probability (p) value threshold; and
    (c) group the list of proteins based on similar profiles, wherein a similar profile is indicative of a functional link between proteins within a genome;
    wherein the comparing is performed by an algorithm, the algorithm is selected from the group consisting of a Smith-Waterman algorithm, Needleman-Wunsch algorithm, BLAST, FASTA, and PSI-BLAST, and the probability value is set with respect to the value 1/NM, based on the total number of sequence comparisons that are to be performed, wherein N is the number of proteins in the first organism's genome and M in all other genomes.

21. A method for identifying pairs of proteins in a genome as being functionally linked, comprising:
    (a) providing a first plurality of protein sequences comprising substantially all protein sequences encoded by a first genome, or, a plurality of nucleic acid sequences comprising substantially all protein-encoding nucleic acid sequences in a first genome;
    (b) providing a second plurality of protein sequences comprising substantially all protein sequences encoded by one or more additional genomes, or, a second plurality of nucleic acid sequences comprising substantially all protein-encoding nucleic acid sequences of one or more additional genomes;
    (c) comparing each protein sequence or nucleic acid sequence in the first plurality of protein sequences or nucleic acid sequences respectively with substantially all the protein sequences or nucleic acid sequences of the second plurality of protein sequences or nucleic acid sequences to determine if the protein sequence or nucleic acid sequence in the first genome has a homolog in the one or more additional genomes based on the degree of similarity of the sequences being compared;
    (d) generating a phylogenetic profile for each protein of the first genome, wherein the phylogenetic profile is a vector or pattern whose elements indicate whether a homolog of the protein or protein encoding nucleic acid sequence of the first genome is present or absent in each of the one or more additional genomes of the second plurality of protein sequences or nucleic acid sequences, and
    (e) linking proteins of the first genome having similar phylogenetic profiles, wherein proteins with similar profiles are identified as being functionally linked;
    wherein the phylogenetic profile is generated in a binary code describing the presence or absence of a given protein in an organism.

22. A computer program, stored on a computer-readable medium, for identifying pairs of proteins in a genome as being functionally linked, the computer program comprising instructions for causing a computer system to:
    (a) provide a first plurality of protein sequences comprising substantially all protein sequences encoded by a first genome, or, a plurality of nucleic acid sequences comprising substantially all protein-encoding nucleic acid sequences in a first genome;
    (b) provide a second plurality of protein sequences comprising substantially all protein sequences encoded by one or more additional genomes, or, a second plurality of nucleic acid sequences comprising substantially all protein-encoding nucleic acid sequences of one or more additional genomes;
    (c) compare each protein sequence or nucleic acid sequence in the first plurality of protein sequences or nucleic acid sequences respectively with substantially all the protein sequences or nucleic acid sequences of the second plurality of protein sequences or nucleic acid sequences to determine if the protein sequence or nucleic acid sequence in the first genome has a homolog in the one or more additional genomes based on the degree of similarity of the sequences being compared;

(d) generate a phylogenetic profile for each protein of the first genome, wherein the phylogenetic profile is a vector or pattern whose elements indicate whether a homolog of the protein or protein encoding nucleic acid sequence of the first genome is present or absent in each of the one or more additional genomes of the second plurality of protein sequences or nucleic acid sequences; and (e) link proteins of the first genome having similar phylogenetic profiles, wherein proteins with similar profiles are identified as being functionally linked.

23. The computer program of claim 22, wherein the protein sequences or nucleic acid sequences are present in one or more databases.

24. The computer program of claim 22, wherein the phylogenetic profile is generated using a bit type profiling method.

25. The computer program of claim 22, wherein the nucleic acid sequence is translated by the computer program to an amino acid sequence.

26. The computer program of claim 22, wherein the comparing is performed by an algorithm.

27. The computer program of claim 26, wherein the algorithm is selected from the group consisting of a Smith-Waterman algorithm, Needleman-Wunsch algorithm, BLAST, FASTA, and PSI-BLAST.

28. The computer program of claim 27, wherein step (c) further comprises determining the significance of the homology of the proteins by computing a probability (p) value threshold.

29. The computer program of claim 22, wherein the phylogenetic profile is in the form of a vector, matrix or phylogenetic tree.

30. The computer program of claim 22, wherein the presence or absence is by calculating an evolutionary distance.

* * * * *